(12) United States Patent
Chtourou et al.

(10) Patent No.: US 10,344,272 B2
(45) Date of Patent: Jul. 9, 2019

(54) RECOMBINANT OR TRANSGENIC FACTOR VII COMPOSITION, EACH FACTOR VII MOLECULE HAVING TWO N-GLYCOSYLATION SITES WITH DEFINED GLYCAN UNITS

(75) Inventors: Abdessatar Sami Chtourou, Elancourt (FR); Emmanuel Nony, Antony (FR); Nicolas Bihoreau, Orsay (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 206 days.

(21) Appl. No.: 12/300,486

(22) PCT Filed: May 31, 2007

(86) PCT No.: PCT/FR2007/000909
§ 371 (c)(1),
(2), (4) Date: Apr. 20, 2009

(87) PCT Pub. No.: WO2007/138199
PCT Pub. Date: Dec. 6, 2007

(65) Prior Publication Data
US 2009/0311239 A1    Dec. 17, 2009

(30) Foreign Application Priority Data

May 31, 2006   (FR) ...................... 0604872

(51) Int. Cl.
*C12N 9/64* (2006.01)
*A61K 38/36* (2006.01)
*C12N 15/85* (2006.01)
*A01K 67/027* (2006.01)
*A61K 38/00* (2006.01)

(52) U.S. Cl.
CPC ........ *C12N 9/6437* (2013.01); *A01K 67/0275* (2013.01); *C12N 15/8509* (2013.01); *C12Y 304/21021* (2013.01); *A01K 2217/05* (2013.01); *A01K 2227/107* (2013.01); *A01K 2267/01* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,229,342 A | 10/1980 | Mirabel | |
| 4,519,945 A | 5/1985 | Ottenhof | |
| 5,344,918 A | 9/1994 | Dazey et al. | |
| 5,827,690 A | 10/1998 | Meade et al. | |
| 5,849,992 A | 12/1998 | Meade et al. | |
| 5,880,327 A | 3/1999 | Lubon et al. | |
| 5,997,864 A | 12/1999 | Hart et al. | |
| 6,046,380 A | 4/2000 | Clark | |
| 6,183,803 B1 | 2/2001 | Morcol et al. | |
| 6,255,554 B1 | 7/2001 | Lubon et al. | |
| 6,268,487 B1 | 7/2001 | Kutzko et al. | |
| 6,399,336 B1 * | 6/2002 | Paulson et al. | .................. 435/97 |
| 6,903,069 B2 | 6/2005 | Pingel et al. | |
| 6,984,772 B1 | 1/2006 | Velander et al. | |
| 7,045,676 B1 | 5/2006 | Gordon et al. | |
| 7,067,713 B2 * | 6/2006 | Nuijens | .............. A01K 67/0278 800/14 |
| 7,247,331 B2 | 7/2007 | Souppe | |
| 2004/0117862 A1 | 6/2004 | Cooper et al. | |
| 2004/0219225 A1 | 11/2004 | Kivits et al. | |
| 2005/0272917 A1 | 12/2005 | Jiao et al. | |
| 2006/0040025 A1 | 2/2006 | Souppe | |
| 2008/0044544 A1 | 2/2008 | Souppe | |
| 2009/0239788 A1 | 9/2009 | Chtourou et al. | |
| 2009/0281283 A1 | 11/2009 | Lejars et al. | |
| 2010/0047428 A1 | 2/2010 | Lejars et al. | |

FOREIGN PATENT DOCUMENTS

| | | |
|---|---|---|
| CA | 2051047 A1 | 3/1992 |
| EP | 0200421 A2 | 12/1986 |
| EP | 0264166 A1 | 4/1988 |
| EP | 0741515 B1 | 11/2003 |
| EP | 0807170 B1 | 3/2006 |
| EP | 01739170 A2 | 1/2007 |
| JP | 504587 A | 12/1990 |
| JP | 5-345799 A | 12/1993 |
| WO | 89/12097 | 12/1989 |
| WO | 95/17085 A1 | 6/1995 |
| WO | 96/03051 A1 | 2/1996 |
| WO | 96/09377 A1 | 3/1996 |
| WO | 01/57079 A2 | 8/2001 |
| WO | 01/58935 A2 | 8/2001 |

(Continued)

OTHER PUBLICATIONS

Grabenhorst, E., et al. 1999 Glycoconjugate Journal 16: 81-97.*
Hiripi, L., et al. 2003 DNA and Cell Biology 22(1): 41-45.*
Koles, K., et al. 2004 Glycobiology 14(1): 51-64.*
Koles, K., et al. 2004 Glycobiology 14(11): 979-986.*
Hagen, FS et al. Characterization of a cDNA coding for human factor VII. Proc. Natl. Acad. Sci. USA. 1986. vol. 83. pp. 2412-2416.
Spiro, R et al. Occurrence of a-D-Galactosyl Residues in the Thyroglobulins from Several Species. Journal of Biological Chemistry. 1984. vol. 259. No. 15. pp. 9858-9866.
Hironaka, T et al. Comparative Study of the Sugar Chains of Factor VIII Purified from Human Plasma and from the Culture Media of Recombinant Baby Hamster Kidney Cells. Journal of Biological Chemistry. 1992. vol. 267, No. 12. pp. 8012-8020.

(Continued)

*Primary Examiner* — Marsha Tsay
(74) *Attorney, Agent, or Firm* — Potomac Law Group PLLC

(57) ABSTRACT

The invention is related to a composition of recombinant or transgenic Factor VII, each molecule of Factor VII of the composition exhibiting two N-glycosylation sites, wherein, among all the molecules of FVII of the composition, the proportion of Galα1,3Gal glycan moieties is comprised between 0 and 4%. The invention is also related to a process for preparing such a composition of FVII.

10 Claims, 11 Drawing Sheets

Specification includes a Sequence Listing.

(56) References Cited

FOREIGN PATENT DOCUMENTS

| | | |
|---|---|---|
| WO | 0229025 A2 | 4/2002 |
| WO | 2004/076695 A1 | 9/2004 |
| WO | 2005024006 A2 | 3/2005 |
| WO | 2005/089040 A2 | 9/2005 |
| WO | 2006/004675 A2 | 1/2006 |
| WO | 2007/138199 A2 | 12/2007 |
| WO | 2008/099077 A2 | 8/2008 |

OTHER PUBLICATIONS

Galili, U et al. One percent of human circulating B lymphocytes are capable of producing the natural anti-Gal antibody. Blood. 1993. vol. 82. 2485-2493.

Prowse, CV et al. Neoantigens and antibodies to factor VIII. Blood Reviews. 1998. vol. 12. pp. 99-105.

Hoist, J et al. Local Application of Recombinant Active-site Inhibited Human Clotting Factor VIIa Reduces Thrombus Weight and Improves Patency in a Rabbit Venous Thrombosis Model. Eur. J. Endovasc. Surg. 1998. vol. 15. pp. 515-520.

Lathe, R et al. Plasmid and bacteriophage vectors for excision of intact inserts. Gene. 1987. vol. 57. pp. 193-201.

Brinster, RL et al. Factors affecting the efficiency of introducing foreign DNA into mice by microinjecting eggs. Proc. Natl. Acad. Sci. USA. 1985. vol. 82. pp. 4438-4442.

Thim, L et al. Amino Acid Sequence and Posttranslational Modifications of Human Factor VIIa from Plasma and Transfected Baby Hamster Kidney Cells. Biochemistry. 1988. vol. 27. pp. 7785-7793.

Jurlander, B et al. Recombinant Activated Factor VII (rFVIIa): Characterization, Manufacturing, and Clinical Development. Seminars in Thrombosis and Hemostasis. 2001. vol. 27. No. 4. 2001. pp. 373-383.

Lubon, H et al. Vitamin K-Dependent Protein Production in Transgenic Animals. Thrombosis and Haemostasis. 1997. vol. 78. No. 1. pp. 532-536. XP009079265. ISSN:0340-6245.

Kumar, HPM et al. Elucidation of N-linked oligosaccharide structures of recombinant human Factor VIII using fluorophore-assisted carbohydrate electrophoresis. Biotechnol. Appl. Biochem. 1996. vol. 24. pp. 207-216. XP009079481.

Aljamali, MN et al. Generation of transgenic mice expressing high levels of activated murine coagulation factor VII. Blood. 2004. vol. 104. No. 11. Part 2. Nov. 2004. p. 398B. XP002421223. ISSN: 0006-4971. Abstract.

Schoenecker, JG et al. Exposure to Topical Bovine Thrombin During Surgery Elicits a Response Against the Xenogeneic Carbohydrate Galactose alpha1-3 Galactose. Journal of Clinical Immunology. 2000. vol. 20. No. 6. pp. 434-444. XP002421224. ISSN:0271-9142.

Devinoy, E. et al. Sequence of the rabbit whey acidic protein cDNA. Nucleic Acids Research. 1988. vol. 16. No. 16. p. 8180.

Bjoern, S et al. Human Plasma and Recombinant Factor VII; Characterization of O-Glycosylations at Serine Residues 52 and 60 and Effects of Site-Directed Mutagenesis of Serine 52 to Alanine. J Biological Chem. 1991. vol. 260. No. 17. pp. 11051-11057.

Bolt, G et al. Posttranslational N-glycosylation takes place during the normal processing of human coagulation factor VII. Glycobiology. 2005. vol. 15. No. 5. pp. 541-547. XP009061442.

Cox, DA et al. Isolation and characterisation of milk growth factor, a transforming-growth-factor-B2-related polypeptide, from bovine milk. Eur. J. Biochem. 1991. 197. pp. 353-358.

Dave, AS et al. Separation of Human Protein C From Components of Transgenic Milk Using Immobilized Metal Affinity Chromatography. Advances in Experimental Medicine and Biology. 2000. Kluwer Academic/Plenum. vol. 471. 2000. pp. 639-647. XP008071126.

Graham, FL et al. Characteristics of a Human Cell Line Transformed by DNA from Human Adenovirus Type 5. J Gen Virol. 1977. vol. 36. pp. 59-72.

Hibbard, LS et al. The Calcium-binding Properties of Bovine Factor V. Journal of Biological Chemistry. 1980. vol. 255. No. 2. pp. 638-645.

Simons, JP et al. Alteration of the quality of milk by expression of sheep β-lactoglobulin in transgenic mice. Nature. 1987. vol. 328. 6. pp. 530-532.

Urlaub, G et al. Isolation of Chinese hamster cell mutants deficient in dihydrofolate reductase activity. Proc Natl Acad Sci USA. Genetics. Jul. 1980. vol. 77. No. 7. pp. 4216-4220.

Waechter, DE et al. Effect of methylation on expression of microinjected genes. Proc Natl Acad Sci USA. Biochemistry. Feb. 1982. vol. 79. pp. 1106-1110.

Wilkins, TD et al. Isolation of Recombinant Proteins From Milk. Journal of Cellular Biochemistry. 1992. Wiley-Lyss. vol. 49. pp. 333-338. XP000611844.

Zhang, X et al. Stable expression of human alpha-2, 6-sialyltransferase in Chinese hamster ovary cells: functional consequences for human erythropoietin expression and bioactivity. Biochimica et Biophysica Acta. 1998. vol. 1425. pp. 441-452.

Eckart Grabenhorst, "Genetic Engineering of Recombinant Glycoproteins and the Glycosylation Pathway in Mammalian Host Cells", Glycoconjugate Journal 16, 81-97 (1999), 17 Pages.

F.O. Castro, "Transgenic Rabbits for the Production of Biologically-Active Recombinant Proteins in the Milk," Genetic Analysis, Biomolecular Engineering, 15 (1999) 179-187.

Japanese Office Action dated Mar. 17, 2014, Japanese Patent Application No. 2009-512641.

Hironaka et al., "Comparative study of the sugar chains of factor VIII purified from human plasma and from the culture media of recombinant baby hamster kidney cells," The Journal of Biological Chemistry, Apr. 25, 1992, vol. 267, No. 12, pp. 8012-8020.

Guo et al., "Casein precipitation equilibria in the presence of calcium ions and phosphates," Colloids and Surfaces B: Biointerfaces, vol. 29, pp. 297-307 (2003).

"Method of extracting one or multiple proteins present in breast milk", Science of Milk, First Edition, pp. 36-43 (1996).

"Calcium Compounds," Chemical Dictionary, Pocket Edition, pp. 554-555 (1963).

Protein I: Separation, Purification and Properties, Japanese Biochemical Society, pp. 122-125 (1990).

Chevreux et al., "N-/O-glycosylation analysis of human FVIIa produced in the milk of transgenic rabbits," Glycobiology, vol. 23, No. 12, pp. 1531-1546, Oct. 2013.

Ludger Ltd., "Ig Glycan Names," www.ludger.com/products, retrieved from the Internet Oct. 24, 2017.

\* cited by examiner

Ratio of the intensity of MOA-HRP staining / intensity of CBB staining (x 100)

SEQUENCE LISTING

```
<160> NUMBER OF SEQ ID NOS: 1

<210> SEQ ID NO 1
<211> LENGTH: 406
<212> TYPE: PRT
<213> ORGANISM: Homo sapiens

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
```

-continued

```
                    100                 105                 110
Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
        130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
                180                 185                 190

His Cys Phe Asp Lys Ile Lys Asn Trp Arg Asn Leu Ile Ala Val Leu
                195                 200                 205

Gly Glu His Asp Leu Ser Glu His Asp Gly Asp Glu Gln Ser Arg Arg
        210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
                275                 280                 285

Asp Arg Gly Ala Thr Ala Leu Glu Leu Met Val Leu Asn Val Pro Arg
        290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
        370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

RECOMBINANT OR TRANSGENIC FACTOR VII COMPOSITION, EACH FACTOR VII MOLECULE HAVING TWO N-GLYCOSYLATION SITES WITH DEFINED GLYCAN UNITS

The present invention is related to a recombinant or transgenic Factor VII obtained in form of a composition of Factor VII, each molecule of Factor VII having two N-glycosylation sites with defined glycan moieties, and to its use as medicament, as well.

Factor VII (FVII) is a vitamin K dependent glycoprotein which in its activated form (FVIIa) takes part in the coagulation process activating the Factor X and the Factor IX in the presence of calcium and of tissue factor. FVII is secreted in form of a single peptide chain of 406 residues, with a molecular weight of about 50 kDa. The FVII contains four distinctive structural domains: the N-terminal γ-carboxylic domain (Gla), two "epidermal growth factor (EGF)-like" domains, and a serine protease domain. The activation of the FVII into FVIIa is characterized by the cleavage of the $Arg_{152}$-$Ile_{153}$ domain (Arginine 152-Isoleucine 153) linkage. The FVIIa is, therefore, a compound with a light chain of 152 aminoacids with a molecular weight of about 20 kDa, and with a heavy chain of 254 aminoacids with a molecular weight of about 30 kDa) linked one to another with a single disulfide bridge ($Cys_{135}$-$Cys_{262}$).

The plasma FVIIa contains several post-translational modifications: the first ten glutamic acids are γ-carboxylated, $Asp_{63}$ is partially hydroxylated, $Ser_{52}$ (Serine 52) and $Ser_{60}$ (Serine 60) are O-glycosylated and carry the Glucose (Xylose)$_{0-2}$ and Fucose patterns, respectively, $Asn_{145}$ (Asparagine 145) and $Asn_{322}$ (Asparagine 322) are N-glycosylated mainly by biantennary bisialylated complex structures.

FVII is used for the treatment of patients suffering from hemophilia, showing a deficiency of Factor VIII (type A hemophilia) or of Factor IX (type B hemophilia), as of patients showing other deficiencies of coagulation factors, for example, a congenital deficiency of FVII. It is, therefore, necessary that concentrates of injectable FVIIa be available.

The most ancient method for obtaining FVIIa concentrates consisted of the purification of FVIIa from plasma proteins resulting from the fractionation.

For that purpose, the document EP 0 346 241 describes the preparation of a FVIIa-enriched fraction, obtained after adsorption then elution of a secondary product of the fractionation of plasma proteins containing the FVII and the FVIIa and other proteins such as Factors IX (FIX), X (FX) and II (FII), particularly the pre-eluate of PPSB (P=prothrombin or FII, P=proconvertin or FVII, S=Stuart Factor or FX and B=antihemophilic Factor B or FIX). The drawback of this process is that the obtained FVII still contains some traces of the other coagulation factors.

Likewise, the document EP 0 547 932 describes a manufacturing process of a high purity FVIIa concentrate substantially free of vitamin-K-dependent factors and of FVIII. The FVII obtained by this process, in spite of its purity, shows a residual thrombogenic activity.

Thus, one of major drawbacks of these processes is that they yield only small amounts of products. It is, moreover, still difficult to obtain a product entirely free of other proteins present in the plasma. Finally, although a number of precautions are being implemented at every stage of the preparation of plasma coagulation factors in order to ensure their viral and bacterial safety (follow-up of blood donors, tests for detecting of known viral and bacterial contaminants, stringent purification and virus inactivating treatments in order to reduce as far as possible the hazard of transmission of blood-born pathogenic agents), nevertheless, all risks of contamination with pathogenic agents are not excluded. In addition, the appearance of a new variant of the Creutzfeldt-Jakob disease gave rise to fears of transmission of unconventional pathogenic agents by blood products. Moreover, the volume of plasma collected from donors remains limited.

Therefore, since the 1980s, the DNA encoding the human Factor VII was isolated (Hagen et al. (1986); Proc. Natl. Acad. Sci. USA; April 83(8):2412-6) and expressed in mammal BHK cells (Baby Hamster Kidney) (document EP 0 200 421). Even if this method of manufacturing of FVII has the advantage to control the medium where the protein of interest is produced, it is known that the hamster cells impart to proteins which they express Galα1,3Gal moieties (Spiro R G et al, J. Biol. Chem, 1984, vol. 259, N° 15, 9858 and Furukawa K. et al., J. Biol. Chem, 1992, vol. 267, N° 12, 8012), the immunogenicity of which has been demonstrated.

It was found that 1% of the circulating human B lymphocytes raise antibodies against the epitope Galα1,3Gal (Galili et al, Blood, 1993, vol. 82, 2485). The epitope and the antibodies form then a complex activating the complement and leading to severe immunity reactions, such as acute transplant rejection following to xenotransplantations. It was shown that 15 to 20% of the hemophiliacs treated with a FVII produced in a hamster cell develop an immune reaction (Prowse C. V et al, Blood Reviews, 1998, vol. 12, 99). This type of immune reaction is tragic in the case of hemophiliacs, because the FVII and FVIII, having turned immunogenic, will cause bleedings which are very difficult to treat.

Thus, it is still necessary to obtain a composition of recombinant or transgenic FVIIa with a reduced immunogenicity, while being as low as possible, and preferably with increased viral safety.

Therefore, the Applicant conducted investigations with the aim to develop a composition of FVII, preferably with increased viral safety, exhibiting a very reduced immunogenicity.

Thus, the invention is related to a composition of recombinant or transgenic Factor VII, each Factor VII molecule of the composition exhibiting two N-glycosylation sites, characterized in that among all the molecules of FVII of the composition, the proportion of Galα1,3Gal glycan moieties is comprised between 0 and 4%.

Surprisingly, the Applicant has discovered that such a proportion of glycan moieties Galα1,3Gal in the FVII of the composition of invention is not immunogenic when used for treating patients.

The FVII of the invention is in form of a composition. Indeed, any FVII, whether plasmatic, recombinant or transgenic, takes the form of a mixture of several proteins of FVII, these proteins differing in particular in that they do not exhibit the same post-translational modifications. This post-translational processing is performed by the cellular organites upon the transfer of the FVII protein within the different cellular compartments. These biochemical modifications deeply modify the protein, in a fashion that the final protein is rather different from the molecule directly encoded by the gene. These chemical modifications contribute to the regulation of the protein activity, and to the localisation, as well. Thus, for the sake of the invention, expressions «FVII» and «composition of FVII» are equivalent.

«Recombinant or transgenic FVII» refers to any FVII resulting from genetic engineering and having post-translational modification features, in particular of above-mentioned glycosylation, that is two N-glycosylation sites with a zero or a very low proportion of Galα1,3Gal in the composition of FVII, or sufficiently low, so as not to be immunogenic. In contrast, the FVII of the invention is not a plasma FVII, that is, it is not a product purified from human or animal plasma.

More particularly, activated FVII refers to any activated FVII resulting from genetic engineering having the above-mentioned post-translational modification features, as well as two O-glycosylation sites with defined glycan moieties, a γ-carboxylation and specific disulfide bridges.

The Galα1,3Gal moiety is a structure consisting of two α1,3-linked galactoses. It is located on the end of the oligosaccharidic antennas of the N-linked structures. This moiety is known to be immunogenic. Indeed, this glycan moiety is lacking in man and in some monkeys, because the gene encoding the enzyme inducing the synthesis thereof (the α1,3galactosyltransferase) was inactivated. Therefore, the administration to man of a protein exhibiting such a moiety induces the appearance of antibodies raised against the so glycosylated protein.

It is therefore highly desirable that such an immunogenic moiety is not to be found in pharmaceutical proteins.

Preferably, the composition is characterized by a lack of glycan moieties Galα1,3Gal in all the molecules of Factor VII being present.

It is understood that this refers to a FVII, the proportion of structures Galα1,3Gal of which is zero or so low that it cannot be distinguished from the background measured with use of presently available analytical devices, or the proportion of which cannot be detected especially by means of the lectin-blot detection method with coloration in the presence of 4-chloro-1-naphtol. This quantification method is set forth in the section «Examples». This expression refers, in equivalent manner, to any recombinant or transgenic FVII, the proportion of Galα1,3Gal of which is close to that of plasma FVII. Whatever the case, the proportion of Galα1, 3Gal in the composition of FVII of the invention is not immunogenic for man.

Conversely, a commercially available recombinant FVII exhibits a detectable proportion of Galα1,3Gal and can, therefore, be distinguished from the background noise using the analytical devices.

Thus, depending upon the used quantification method, the Galα1,3Gal moiety could be either entirely lacking, or present in an amount less than 4%, or less than 3.5%, or in an amount less than 3%, this amount not being possible to distinguish from the background noise. Advantageously, the Galα1,3Gal moiety is present at an identical or nearly identical proportion to that of the plasma FVII.

The FVII of the invention is a polypeptide the peptide sequence of which can be that of the natural human FVII, that is the sequence present in man is not exhibiting disorders bound to FVII. Such a sequence can be encoded, for example, by the sequence 1b described in the document EP 0 200 421.

Advantageously, the sequence of FVII of the invention is the sequence SEQ ID NO: 1.

In a further embodiment, the FVII of the invention can be a variant of the natural human FVII, insofar that the immunogenicity thereof is not greater than that of the natural FVII. Thus, the peptide sequence of this variant can exhibit at least 70% identity, and advantageously, at least 80% or 90%, and more advantageously at least 99% identity with the sequence of the natural human FVII, such a variant having substantially the same biological activity as the natural FVII.

Moreover, the FVII of the invention refers also to any FVII the biological activity of which was modified or reduced by comparison with that of the natural FVII. By way of example, the recombinant human inactivated FVII, FFR-FVIIa, used for treatment or prophylaxy of thromboses (Holst et al, Eur. J. Vasc. Endovasc. Surg., 1998 June, 15(6): 515-520), can be mentioned. Such FVII are polypeptides having an aminoacid sequence which differs from the sequence of the natural FVII by insertion, deletion or substitution of one or more aminoacids.

Finally, in a further embodiment, the FVII of the invention can be activated (FVIIa). The FVIIa exhibits a coagulation activity 25 to 100 times greater than that of FVII when the latter interacts for and on behalf of the former with the tissue factor (TF). The activation of the FVII results from the cleavage of the zymogen by different proteases (FIXa, FXa, FVIIa) in two chains linked by a disulfide bridge. FVIIa is the coagulation factor responsible for hemostasis in hemophiliacs with circulating antibodies, for example. In a particularly advantageous manner, the FVII of the invention is entirely activated.

The FVIIa of the invention can include several post-translational modifications the first nine or ten N-terminal glutamic acids are γ-carboxylated, $Asp_{63}$ is partially hydroxylated, $Ser_{52}$ and $Ser_{60}$ are O-glycosylated and carry the Glucose(xylose)$_{0-2}$ and Fucose moieties, respectively, $Asn_{145}$ and $Asn_{322}$ are N-glycosylated mainly with biantennary monosialylated complex structures.

The biological activity of the FVII of the invention can be quantified by measuring the capability of a composition of FVII to trigger the blood coagulation by means of a FVII-deficient plasma and the thromboplastin as, for example, described in the U.S. Pat. No. 5,997,864. In the assay described in this patent, the biological activity is expressed by a reduction of the coagulation time compared to the control sample, and is converted into «units of FVII» by comparison with a standard of human serum (pool) containing 1 unit/ml activity of FVII.

The recombinant FVII of the invention can be obtained by use of standard techniques, known to those skilled in the art, allowing the expression of a protein in a biological system.

The FVII of the invention can be expressed in any microorganism, plant or animal conferring the above-mentioned glycosylation features, that is a very low or zero proportion of Galα1,3Gal in the composition of FVII. Microorganism refers to any bacterial, fungal, viral or cell system, the cells could be plant or mammal cells. The mammal cells can be animal or human cells. Use can also be made of any KnockOut cell for the α1,3galactosyltransferase.

The FVII of the invention can also be produced in transgenic animals or plants, insofar these animals or plants confer to the FVII or to the composition of FVII the above-mentioned glycosylation features, namely an absence or a very low proportion of Galα1,3Gal in the composition of FVII. The animals can be rabbit, pig, sheep, goat, beef, chicken, or any KnockOut animal for the α1,3galactosyltransferase, this list not being limitative.

The FVII of the invention contains, like the human FVII, two N-glycosylation sites, in positions 145 and 322, and 2 O-glycosylation sites, in positions 52 and 60. In one N-glycosylation site, the oligosaccharide chains are linked to an asparagine (N-linked). In the O-glycosylation site, the oligosaccharide chains are linked to a serine. The moieties linked to these aminoacids will be different for each protein of the composition. It is, however, possible to quantify, for the whole composition, the amount of every glycan moiety, or of every sugar.

The percentage of the different glycans given in the present application does not take into account the O-glycosylation.

Preferably, the composition of FVII is characterized in that, among all the glycan moieties of the FVII of the composition, at least 40% are biantennary, monosialylated, glycan forms. In a further embodiment, the monosialylated forms are present to at least 50%. In a further embodiment, the monosialylated forms are present to at least 60%.

Advantageously, the glycan forms of the FVII are in majority biantennary monosialylated glycan forms.

The composition of FVII is characterized in that at least some sialic acids of Factor VII imply α2-6 links.

Advantageously, at least 65% of the sialic acids of the FVII imply α2-6 links. More advantageously, at least 70%, or 80%, and, in particular, at least 90% of the sialic acids of the FVII imply α2-6 links.

According an embodiment of the invention, all the sialic acids of Factor VII imply α2-6 links, i.e. that all the sialic acids are bound to galactose by a α2-6 link. The FVII of the composition of the invention can further include sialic acids implying α2-3 links.

The fact that at least 65% of the sialic acids of FVII of the composition imply α2,6 ramifications is one of the advantages of the FVII of the invention. As a matter of fact, the sialic acids of the commercially available recombinant FVII imply α2,3 links only. Whereas, the plasma FVII is a mixture of these two isomers. However, the latter contains more α2,6 links, what brings even closer the FVII of the invention to plasma FVII. According to the invention, from 65% to 100% of the sialic acids of FVII imply α2,6 links. In some embodiments, from 70% or 80% to 100% of the sialic acids of FVII imply α2,6 links.

Advantageously, among the biantennary, monosialylated glycan forms of the FVII, the majority are non-fucosylated.

Preferably, these biantennary, monosialylated, non-fucosylated, glycan forms are present in the FVII of the composition of the invention at a proportion of greater than 20%. Advantageously, this proportion is higher than 25%, or higher than 40%.

In a particularly advantageous way, the proportion of fucosylation of the composition of FVII of the invention is comprised between 20% and 50%. In an embodiment of the invention, this proportion can be less than 15%.

This feature is one of the advantages of the FVII of the invention. Indeed, the commercially available recombinant FVII exhibits a fucosylation proportion of 100%, whereas the plasma FVII has a fucosylation proportion of about 16%. Thus, the fucosylation of the FVII of the invention is close to that of the plasma FVII, which gives an advantage to the FVII of the invention in terms of immunogenicity.

Advantageously, the FVII of the invention is a transgenic FVII. Thus, the FVII of the invention is advantageously a transgenically produced recombinant FVII product.

In a particular embodiment of the invention, the transgenic FVII of the invention is produced in the milk of a transgenic animal.

Such a production of proteins can be carried out by grafting the gene encoding the protein of interest on the regulatory region of one of the genes responsible for the synthesis of milk proteins, which will direct the synthesis specifically in the mammary gland, then its secretion into the milk.

In a particularly advantageous manner, the FVII of the invention is produced by the transgenic female rabbits.

This species is particularly advantageous because the rabbit does not appear to be sensitive to prions, in particular to the transmissible subacute spongiform encephalopathy, which is a major public health issue.

Further, the species barrier between rabbit and man is important. Conversely, the species barrier between man and hamster, which is the biological system where the commercially available recombinant FVII is produced, is less important.

Thus, the production of FVII in rabbit is advantageous in terms of safety with regard to the transmission of pathogenic agents.

In a preferred embodiment of the invention, the FVII of the invention is produced in the mammary glands of female rabbits.

The secretion of the protein of interest from mammary glands, allowing the secretion into the milk of a transgenic mammal, is a well known technique to those skilled in the art implying the control of the expression of the recombinant protein in a tissue-dependent manner.

The tissue control of the expression is carried out thanks to sequences allowing to direct the protein expression towards a particular tissue of the animal. These sequences are namely promoter sequences and peptide signal sequences, as well.

Examples of promoters driving the expression of a protein of interest in mammary glands are the WAP promoter (whey acidic protein), the casein promoter, for example the β-casein promoter, the β-lactoglobulin promoter, this list is not being limitative.

A production method of a recombinant protein in the milk of a transgenic animal can include the following steps: a synthetic DNA molecule comprising a gene encoding the human FVII, this gene being under the control of a promoter of a naturally secreted protein into the milk, is integrated into the embryo of a non-human mammal. Afterwards, the embryo is placed into a mammal female of same species. Once the mammal, obtained from the embryo, is sufficiently developed, the lactation of the mammal is induced, next, the milk is collected. Then the milk contains the transgenic FVII of interest.

An example of a process for preparing protein in the milk of a mammal female other than man is described in the document EP 0 527 063, the teaching of which can be referred to for the production of the protein of interest of the invention, this example not being limitative.

A plasmid containing the WAP promoter is prepared by introduction of a sequence including the promoter of the WAP gene, this plasmid is prepared in a way to be capable to receive a foreign gene placed under the dependence on the WAP promoter. The gene encoding the human FVII is integrated, and placed under the dependence of the WAP promoter. The plasmid containing the promoter and the gene encoding the protein of interest are used for obtaining transgenic female rabbits by microinjection into the male pronucleus of rabbit. Afterwards, the embryos are transferred into the oviduct of hormonally prepared females. The presence of the transgenes is revealed by Southern blot from the DNA extracted from the obtained transgenic young rabbits. The concentrations in the milk of the animals are evaluated by specific radioimmunologic assays.

The transgenic FVII produced by the female rabbit in its milk is obtained in form of a composition where each molecule of Factor VII of the composition exhibits two N-glycosylation sites, characterized in that among all the molecules of FVII of the composition, the proportion of Galα1,3Gal glycan moiety is less than 4%, or even zero. Thus, advantageously, the transgenic FVII produced by the female rabbit does not contain Galα1,3Gal glycan moieties.

Preferably, the composition of transgenic FVII of female rabbit of the invention is characterized in that among all the glycan moieties of the composition, at least 40% are biantennary, monosialylated glycan forms. In a further embodiment, the monosialylated forms are present to at least 50%. In a further embodiment, the monosialylated forms are present to at least 60%.

Advantageously, the majority of the glycan forms are biantennary, monosialylated glycan forms.

The composition of FVII is characterized in that at least some sialic acids of Factor VII imply α2-6 links.

Advantageously, at least 65% of the sialic acids of the FVII imply α2-6 links. More advantageously, at least 70%, or 80%, and, in particular, at least 90% of the sialic acids of the FVII imply α2-6 links.

According an embodiment of the invention, all the sialic acids of Factor VII imply α2-6 links, i.e. that all the sialic acids are bound to galactose by a α2-6 link. The FVII of the composition of the invention can further include sialic acids implying α2-3 links.

Preferably, among the biantennary, monosialylated glycan forms, the majority of glycan forms are non-fucosylated. Advantageously, these biantennary, monosialylated non-fucosylated glycan forms are present in the FVII of this composition at a proportion higher than 20%. Advantageously, this proportion is greater than 25%, or higher than 40%.

Preferably, the fucosylation proportion of the FVII of this composition of the invention is comprised between 20% and 50%.

In an embodiment of the invention, this proportion can be less than 15%.

The transgenic FVIIa of the invention can include several post-translational modifications: the first nine or ten N-terminal glutamic acids are γ-carboxylated, $Asp_{63}$ (Asparagine 63) is partially hydroxylated, $Ser_{52}$ (Serine 52) and $Ser_{60}$ (Serine 60) are O-glycosylated and carry the Glucose(Xylose)$_{0-2}$ and Fucose moieties, respectively, $Asn_{145}$ and $Asn_{322}$ are N-glycosylated mostly by biantennary monosialylated complex structures.

The FVII of the invention can be purified from the milk by techniques known to those skilled in the art. For example, a method of purification of a protein of interest from milk, such as described in the U.S. Pat. No. 6,268,487, can include the following steps consisting of: a) subjecting the milk to a tangential filtration on a membrane having a porosity sufficient to form a retentate and a permeate, the permeate containing the exogenous protein, b) subjecting the permeate to a capture apparatus by chromatography in order to displace the exogenous protein and to obtain an effluent, c) combining the effluent and the retentate, d) repeating the steps a) to c) until the FVII is separated from the lipids, casein micelles, and the FVII is recovered to at least 75%.

Advantageously, the FVII of the invention is activated. The FVIIa results, in vivo, from the cleavage of the zymogen with different proteases (FIXa, FXa, FVIIa) in two chains linked by a disulfide bridge. The FVIIa itself has a very low enzymatic activity, but complexed with its cofactor, the tissue factor (TF), it triggers the process of coagulation by activating the FX and the FIX.

The FVIIa of the invention is therefore a compound consisting of a light chain of 152 aminoacids with a molecular weight of about 20 kDa and of a heavy chain of 254 aminoacids with a molecular weight of about 30 kDa linked by a single disulfide bridge ($Cys_{135}$-$Cys_{262}$).

Thus, the FVII of the invention is an activated FVII having an activity and a structure close to the plasma FVII.

The FVIIa exhibits a coagulation activity 25 to 100 times greater than that of FVII upon their interaction with the tissue factor (TF).

In an embodiment of the invention, the FVII can be activated in vitro by the Factors Xa, VIIa, IIa, IXa and XIIa.

The FVII of the invention can also be activated during the process of its purification.

The Applicant has surprisingly noticed that the FVII, even when placed under the control of a promoter of a protein naturally produced in the lactoserum, for example, the WAP promoter, is nevertheless liable to be associated with calcium ions of the milk, and therefore with casein micelles.

Thus, the development of a process for extraction and purification of FVII, liable to capture this protein whether associated in the lactoserum complexes or engaged in the casein micelles, the FVII exhibiting an affinity for the calcium ions of the milk, will be very advantageous.

For example, a process for extraction and purification of transgenic FVII, contained in milk of a transgenic animal, includes the following steps consisting of:
a) extracting of the FVII from the milk, the Factor VII being bound to organic and/or inorganic salts and/or complexes of calcium of the said milk, by precipitation of calcium compounds obtained by addition of a soluble salt to the milk, the anion of which is selected for its capability to form said insoluble calcium compounds in order to release in this way the Factor VII from said salts and/or complexes, the Factor VII being then present in a liquid phase,
b) separating of the protein-enriched liquid phase from the precipitate of calcium compounds, said liquid phase being further separated in a lipidic phase and in an aqueous nonlipidic phase containing the protein,
c) subjecting the aqueous nonlipidic phase to an affinity chromatography step, using an elution buffer based on a phosphate salt in a predetermined concentration, and
d) subjecting the eluate of Factor VII, obtained according to the step c), to two or three chromatography steps on a weak basic type anion exchange columns using buffers suitable for successive elutions of the Factor VII retained on said columns.

The Applicant has surprisingly noticed that such a process makes use of an extraction step of the FVII bound to organic and/or inorganic salts and/or complexes of calcium of said milk by precipitating the insoluble calcium compounds obtained by addition of a soluble salt to the milk, the anion of which is selected for its capability to form precipitates of calcium compounds, whereas the FVII is released from these organic and/or inorganic salts and/or complexes and/or organic and/or inorganic complexes of calcium of the said milk and is found again in solution in the liquid phase.

The FVII is bound to organic and/or inorganic salts and/or complexes of calcium of said milk, what means that the FVII exhibits an affinity for these salts and/or complexes of calcium. Therefore, the FVII exhibits a sufficient number of sites of fixation to these salts and/or complexes to be, totally or partially, bound.

Organic and/or inorganic salts and/or complexes of calcium of the milk represent the phosphocalcic salts interacting with the colloidal casein micelles. The different caseins form a colloidal micellar complex, able to reach diameters of about 0.5 µm, with phosphocalcic salts which are present, for example, in form of aggregates («clusters») of tricalcium phosphate, that is $Ca_9(PO_4)_6$. Such micelles are formed from casein sub-units consisting of casein-κ-rich hydrophilic layer surrounding the hydrophobic nucleus, the phosphocalcic salts are bound by electrostatic interactions on a hydrophilic layer. These phosphocalcic salts can also be present in the internal volume of the micelle without being bound to the casein. These salts and/or complexes are also present in the milk in form of monocalcium phosphate and/or dicalcium phosphate, which are in equilibrium with the other ionic forms of calcium depending upon the implemented chemical and biochemical reactions. These calcium salts and/or complexes can be present in the internal volume of the micelle of casein.

Such an affinity of the FVII for the organic and/or inorganic salts and/or complexes of calcium can result from interactions of the non modified or in vivo or in vitro modified protein, for example, by post-translational modifications.

In the process of the invention, the transgenic FVII represents any transgenic FVII exhibiting diverse properties, in particular concerning glycosylation. Advantageously, it is the FVII of the invention, as defined hereinabove.

Insoluble calcium compounds refers to calcium salts or complexes having a solubility of less than 0.5% in the milk.

The majority of FVII is associated with phosphocalcic salts of the casein micelles. The FVII exhibits a strong affinity for the calcium, with a high affinity constant, that is at least 70% to 90% of the FVII are trapped in the casein micelles. The remaining FVII exhibits an affinity for the other forms of the above-mentioned organic and/or inorganic salts and/or complexes of calcium.

Not being bound to any interpretation of the observed mechanisms, the Applicant assumes that the addition of the soluble salt displaces the equilibrium of the phosphocalcic salts of the micelles, causing thus their destructuration, and the precipitation of aggregates of the casein sub-units. The FVII associated with the phosphocalcic salts trapped in and/or on the micelles is released into the medium upon this destructuration. In addition, at the same time, the FVII is also released or dissociated from the phosphocalcic salts, because they precipitate in form of insoluble calcium compounds under the effect of the soluble salt used in the process of the invention. Likewise, the FVII associated with soluble organic and/or inorganic salts and/or complexes of calcium will also be dissociated by the same type of reaction (See FIG. 9).

In the scope of the invention, the soluble salt is any salt allowing to obtain the desired effect.

The soluble salt used in the process of the invention can be present in the milk in a concentration selected by those skilled in the art in order to succeed the separation of FVII from the salts and/or complexes of calcium. As a matter of fact, this concentration is sufficient to allow the separation of at least 20%, or advantageously of at least 30% to 50% of FVII. In a particularly advantageous way, it is a concentration sufficient to allow the separation of at least 60% to 80%, or of at least 90% of the FVII.

The process of the invention allows the precipitation especially of the aggregates of casein sub-units. This precipitation is due to the destructuration of the casein micelles, as mentioned above. The applied process of the invention destabilizes, by precipitation, the colloidal state of the milk.

Therefore, the process of the invention is a process allowing the passage of the milk from a colloidal state to a liquid state, what corresponds to a direct extraction of colloids/liquids.

The process of the invention also allows to obtain the lactoserum with a lighter coloration than that of the starting milk. As a matter of fact, these are the caseins which confer their white color to the milk. Once precipitated, they are not able anymore to confer their color to the milk.

Soluble salt according to the invention refers to a salt with a solubility in the milk of at least 0.5 parts of salt per part of milk (w/w).

Advantageously, the soluble salt used in the process is a phosphate salt. The salt can be in an aqueous solution which is subsequently added to the milk, or in powder form which can be added directly to the milk.

Preferably, the phosphate salt is selected from the group consisting of sodium phosphate, lithium phosphate, potassium phosphate, rubidium phosphate and cesium phosphate, and is, particularly, sodium phosphate.

Alternatively, the soluble salt used in the process of the invention can be an alcali metal oxalate, particularly sodium or potassium oxalate, or an alcali metal carbonate, particularly, sodium or potassium carbonate, or a mixture thereof.

Advantageously, the concentration of the soluble salt in aqueous solution, prepared in order to carry out the process, is comprised between 100 mM and 3 M, more preferably, comprised between 200 mM and 500 mM and, in particular, comprised between 200 mM and 300 mM.

The milk containing the FVII to be extracted can be raw whole milk or skimmed milk. The advantage of applying the process of the invention to skimmed milk lies in the fact that the lipid content thereof is lower. The process can also be applied to fresh or frozen milk.

The process includes a step b) of separation of the liquid phase in a lipidic phase and in an aqueous nonlipidic phase comprising the protein, which is preferably carried out by centrifugation. The nonlipidic aqueous phase is actually the lactoserum. This separation step also allows to isolate the aggregates of casein micellary sub-units and the precipitate of calcium compounds.

The process can further include, after the separation step, a filtration step of the nonlipidic aqueous phase carried out successively on filters with a decreasing porosity, preferably, of 1 μm, then of 0.45 μm. The use of these filters, such as on glass fibers basis, allows to reduce the content of lipids, fat globules and phospholipids naturally present in the milk. A porosity of less than 0.5 μm of the filters allows to maintain the bacteriological quality of the nonlipidic aqueous phase and of the later implemented purification supports (ultrafilters, chromatography columns, etc.) (see hereafter). The lipidic phase is preferably filtered through these filters which retain completely the fat globules of the milk, and the filtrate is clear.

This step can be followed by a step of concentration/dialysis by ultrafiltration.

The concentration allows to reduce the volume of the nonlipidic aqueous phase in order to preserve it. The ultrafiltration membrane is selected by those skilled in the art depending upon the characteristics of the protein of interest. Generally, a porosity limit with pore size less or equal to the molecular weight of the FVII allows to concentrate the product without noteworthy losses. For example, a membrane with a pore size to 50 kDa allows to concentrate without loss the FVII with a molecular weight of 50 kDa.

The dialysis is intended to the conditioning of the nonlipidic aqueous phase comprising the FVII for the subsequent purification steps, namely by chromatography. The dialysis also allows to remove the small molecular size components, such as lactoses, salts, peptides, proteoses-peptones and any agent liable to damage the preservation of the product. To this end, use is made preferentially of a membrane having a retention limit of 50 kDa, so that the FVII is not filtered through the membrane.

Preferably, the dialysis buffer is a 0.025 M-0.050 M solution of sodium phosphate, pH 7.5-8.5.

The nonlipidic aqueous phase obtained after the step b) or, if the case arises, such as obtained after the steps of filtration and/or concentration/dialysis, can be frozen and stored at a temperature of −30° C. prior to performing of subsequent purification steps.

Afterwards, the nonlipidic aqueous phase obtained according to the step b) is subjected to a step c) of affinity chromatography carried out using standard chromatographic devices, and advantageously implemented on a chromatographic column, the support of which is a hydroxyapatite gel ($Ca_{10}(PO_4)_6(OH)_2$) or a fluoroapatite ($Ca_{10}(PO_4)_6F_2$) gel. Thus, the FVII of the aqueous phase is retained on the support, the major part of the not-retained lactic proteins are eliminated.

Preferably, use is made of a chromatographic column which is equilibrated with an aqueous buffer A based on 0.025 M-0.035 M sodium phosphate, pH 7.5-8.5. The FVII-enriched aqueous phase is injected onto the column, what allows to retain the FVII. The not-retained fraction is removed by percolation of the buffer A until return to baseline (RBL) ensuring a good removal of the undesired compounds, such as the lactic proteins. Measurements of the absorbance are performed at a wavelength ($\lambda$) of 280 nm.

The elution of FVII according to the step c) is carried out with an buffer based on a phosphate salt, such as sodium or potassium phosphate or a mixture thereof, with a predetermined concentration, preferably representing a buffer B based on 0.25 M-0.35 M sodium phosphate, pH 7.5-8.5. The eluted fraction is collected up to RBL. Measurements of the absorbance are performed at a wavelength ($\lambda$) of 280 nm.

Thanks to this step, more than 90% of all the lactic proteins are removed and more than 90% of the FVII are recovered. The purity of this eluted fraction of FVII in this stage is about of 5%.

The purity is defined as the weight ratio between the FVII and the total proteins present in the considered sample, the fraction or the eluate.

Advantageously, the specific activity of the FVII is increased by a factor 10 to 25 as a result of the affinity of FVII for the chromatographic support.

Afterwards, the eluate of FVII resulting from the step c) is advantageously subjected to a tangential filtration.

The tangential filtration membrane is selected by those skilled in the art depending on the characteristics of the FVII. Generally speaking, a porosity limit with pores of a size two times greater than the molecular weight of the FVII allows the filtration thereof. Therefore, a membrane with pores of a size of 100 kDa allows the filtration of the FVII with good yields.

The aim of this step of filtration is to reduce the load especially of proteins with molecular weight higher than that of FVII and, particularly, to remove the atypical forms of FVII (for example of FVII in polymerised form), and the proteases which are liable to degrade it within a certain delay. To this end, use is very advantageously made of a membrane with a porosity limit of compounds of 100 kDa.

Advantageously, the filtered eluate of FVII obtained is further concentrated and dialyzed by ultrafiltration through membranes with a retention limit of 50 kDa. The dialysis buffer is preferably a 0.15 M-0.20 M sodium chloride solution.

The eluate of FVII obtained at the end of the step c), optionally filtered, concentrated and dialyzed, is then subjected to two or three chromatography steps (step d)) on weak basic type anion exchange columns using suitable buffers for the subsequent elutions of Factor VII retained on said columns. These steps allow an additional purification of the FVII, in particular with respect to lactic proteins. These steps are implemented with standard chromatographic devices.

The first anion exchange chromatography step is advantageously carried out by use of a Q-Sepharose® FF gel type chromatographic support which retains the Factor VII, depending upon the following preferential operating conditions. This support is washed with a buffer 0.05 M Tris, pH 7.0-7.5. The not-retained fraction is removed with the washing buffer until the return to baseline. The elution of the FVII is performed with an aqueous buffer based on 0.05 M Tris and 0.020 M-0.05 M, preferably 0.05 M, calcium chloride, pH 7.0-8.0, in order to obtain the first eluate of Factor VII. Measurements of the absorbance are performed at a wavelength ($\lambda$) of 280 nm.

The recovery of the FVII in this step is of at least 70% and this allows to remove about 80% of associated proteins, especially milk proteins.

Afterwards, the eluate of FVII can be subjected to a dialysis step, as described previously, using a solution 0.15-0.20 M sodium chloride as buffer.

The second chromatographic step is advantageously carried out on a Q-Sepharose® FF gel type chromatographic support, onto which is injected the first eluate of FVII, obtained in the first chromatographic step on anion exchanger, depending upon the following preferential operating conditions. The support is washed with a 0.05 M, pH 7.0-7.5 Tris buffer. The not-retained fraction is removed with the washing buffer until the return to baseline. Detection is performed through absorbance at $\lambda$=280 nm.

The elution of FVII, retained on the support, is performed with an aqueous buffer based on 0.05 M Tris and 0.005 M calcium chloride, pH 7.0-8.0, in order to obtain a second eluate of high purity Factor VII, that is with a purity higher than 90%. Measurements of the absorbance are performed at a wavelength ($\lambda$) of 280 nm.

The second chromatographic step is intended to limit a possible proteolytic degradation of the protein.

At this stage, the purity of the eluate is of about 90%, and more than 95% of the remaining associated proteins are eliminated. Afterwards, the eluate can be subjected to a dialysis step, as described previously, using a 0.15-0.20 M solution of sodium chloride as buffer.

According to a very preferred implementation of the invention, the process includes three chromatographic steps on weak basic type anion exchanger columns using suitable buffers for the successive elutions of Factor VII from said columns. Thus, after the two above-mentioned anion exchange chromatographies, a third anion exchange chromatography step is performed. This step allows to formulate the protein-enriched composition, in a way to be adapted to medical use.

The third chromatographic step is advantageously carried out on a Q-Sepharose® FF gel type chromatographic support, onto which is injected the second eluate of FVII obtained in the second chromatographic step on anion exchanger, depending upon the following preferential operating conditions.

The second eluate, obtained by the second anion exchange chromatography step is injected, preferably after dilution with 1 to 5 volumes of purified water for injection (WFI), onto a column packed with a Q-Sepharose® FF de type support which retains the Factor VII. This support is washed with a buffer 0.05 M Tris, pH 7.0-7.5. The not-retained fraction is eliminated with the washing buffer until the RLB. Measurements of the absorbance are performed at a wavelength (λ) of 280 nm.

The elution of FVII, retained on the support, is performed with an aqueous buffer based on 0.02 M Tris and 0.20-0.30 M, preferably 0.28 M, sodium chloride, pH 6.5-7.5. Measurements of the absorbance are performed at a wavelength (λ) of 280 nm.

The purity of the thus obtained composition of transgenic FVII is greater than 95%. Very advantageously, the composition appears in form of a concentrate of FVII.

The implementation of the process leads to a cumulated yield of 20 to 25% allowing the purification of at least 20 mg of FVII/liter of treated milk.

Consequently, the three chromatographic steps on an anion exchanger gel allow to further purify the FVII. Moreover, they allow to concentrate and to formulate the composition of FVII.

The activation of FVII occurs during the process, in all probability during the first step of the anion exchange chromatography.

Once the last eluate is recovered, said eluate could be submitted to a filtration step on 0.22 μm filters, to a distribution step in containers and then freezed to −30° C. and stored at this temperature.

The process of the invention can also include at least one of the following steps of formulation, virus inactivation and sterilization. Generally speaking, the process can include, prior to the affinity chromatography step, an anti-viral treatment step which is advantageously carried out by solvent/detergent, in particular in the presence of a mixture of Tween® 80 (1% w/v) and TnBP (tri-n-butylphosphate) (0.3% v/v,), leading to the inactivation of enveloped viruses. Moreover, the eluate of FVII obtained from the second chromatographic step on anion exchanger is preferably subjected to a nanofiltration step in order to eliminate efficiently the viruses, in particular the non-enveloped viruses, such as the parvovirus B19. It is possible to use ASAHI PLANOVA™15 filters retaining the viruses with a size greater than 15 nm.

A further object of the invention is the composition of FVII of the invention for use as medicament.

A further object of the invention is the use of the composition of FVII according to the invention for preparing a medicament intended to the treatment of patients suffering from haemophilia.

A further object of the invention is the use of the composition of FVII according to the invention for preparing a medicament intended to the treatment of multiple hemorrhagic trauma.

A further object of the invention is the use of the composition of FVII according to the invention for preparing a medicament intended to the treatment of massive uncontrollable bleedings by surgical hemostasis.

A further object of the invention is the use of the composition of FVII for preparing a medicament intended to the treatment of bleedings or hemorrhages due to an overdose of anticoagulants.

A further object of the invention is a pharmaceutical composition comprising the Factor VII according to the invention and a pharmaceutically acceptable excipient and/or carrier.

The excipient can be any solution, such as a saline, physiologic, isotonic or buffered solution, and any suspension, gel or powder, as well, compatible with a pharmaceutical use and known to those skilled in the art. The compositions according to the invention can further contain one or more agents or carriers selected among dispersers, solubilizers, stabilizers, surfactants and conservers. On the other hand, the compositions according to the invention can contain further agents or active principles.

Moreover, the compositions can be administered in different ways and in different forms. The administration can be given by any classical route for this type of therapeutic approach, such as especially by systemic route, particularly by intravenous, intradermal, intra-tumor, subcutaneous, intra-peritoneal, intramuscular or intra-arterial injection. For example, the intra-tumor injection or the injection in a zone near to the tumor or irrigating the tumor, can be mentioned.

The doses can vary depending upon the number of administrations, the association with other active principles, the degree of evolution of the pathology, etc.

Further aspects and advantages of the invention will be described by the following examples, which are intended to illustrate and non to limit the scope of the invention.

ABBREVIATIONS USED FOR THE EXAMPLES

FVII-tg=FVIIa-tg: activated transgenic FVII according to the invention
FVII-rec=FVIIa-rec: commercially available recombinant activated FVII
FVII-pd=FVIIa-pd: activated FVII of plasma origin, that is purified from human plasma.
MALDI-TOF: Matrix Assisted Laser Desorption Ionisation—Time of Flight
HPCE-LIF: High Performance Capillary Electrophoresis-Laser Induced Fluorescence
ESI-MS: Mass spectrometry-Electrospray Ionisation
LC-ESIMS: Liquid chromatography-Mass spectrometry-Electrospray Ionisation
NP-HPLC: Normal Phase High Performance Liquid Chromatography
PNGase F: Peptide: N-glycosidase F
LC-MS: Liquid Chromatography-Mass spectrometry

EXAMPLES

Figure 1:
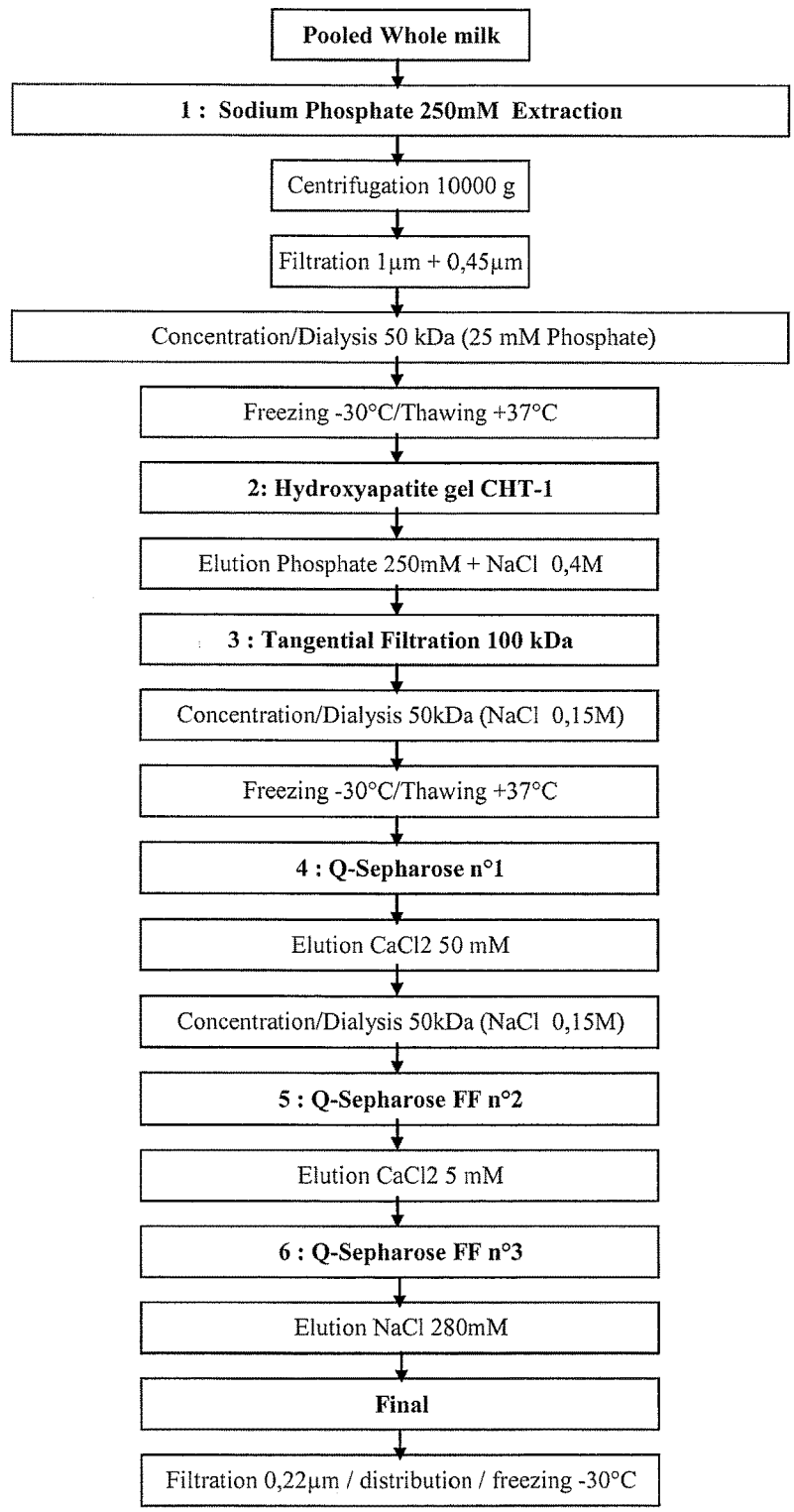
FIG. 1: outline of an example of the extraction and purification/activation process of the transgenic FVII according to the invention produced in the milk of female rabbit.

Example 1: Production of Transgenic Female Rabbits Producing a Human FVII Protein in Their Milk First, a plasmid p1 is prepared by introduction of the sequence Bam H1-Hind III (6.3 Kb fragment) of the WAP gene (described in the document Devinoy et al, Nucleic Acids Research, vol. 16, no. 16, 25 Aug. 1988, p. 8180) in the polylinker of the p-poly III-I vector (described in the document Lathe et al, Gene (1987) 57, 193-201), between the sequences Bam H1 and Hind III.

In the process of this cloning, the site Bam H1 was suppressed and replaced by the site Cla I which is present in the vector p1. The vector p1 is therefore a plasmid able to receive a foreign gene placed under the dependence of the 6.3 Kb WAP promoter. The introduction of the foreign gene can be carried out, for example, into the site Sal I of the polylinker. The inserts containing the totality of the promoter and of the foreign genes can be isolated from the plasmid after cutting in two sites Not 1 which are at the ends of the polylinker of the p-poly III-I plasmid.

The plasmid p2, obtained from the plasmid p1, contains the promoter of the WAP gene of rabbit (6.3 Kb) and the gene of the human FVII. The fragment used for obtaining the transgenic female rabbits is contained between the two sites Not1.

A site Hind III was introduced into the leader sequence of the gene by site specific mutagenesis in order to be used as cloning site.

The transgenic female rabbits were obtained by classical microinjection technique (Brinster et al, Proc. Natl. Acad. Sci. USA (1985) 82, 4438-4442). 1-2 pl containing 500 copies of the gene were injected into the male pronucleus of mouse embryos. The constructions were carried out in the p-poly III-I vector (Lathe et al, Gene (1987) 57, 193-201). The fragments Not 1—Not 1 of this vector containing the recombined genes were microinjected. Afterwards, the embryos were transferred into the oviduct of hormonally prepared adoptive females. About 10% of the manipulated embryos gave birth to young rabbits and 2-5% of the manipulated embryos to transgenic young rabbits. The presence of the transgenes was revealed by Southern transfer technique from the DNA extracted from rabbit tails. The concentrations of FVII in the blood and in the milk of animals were evaluated by specific radioimmunological assays.

The biological activity of the FVII was evaluated by addition of milk to the cellular or rabbit mammal explants culture medium.

The technique employed for obtaining transgenic female rabbits producing the FVII of the invention in their milk, is described in more details in the document EP 0 527 063.

Example 2: Extraction and Purification of the Obtained FVII a) Extraction of the FVII 500 ml of raw whole milk are taken and diluted with 9 volumes of 0.25 M sodium phosphate buffer, pH 8.2. After stirring for 30 minutes at room temperature, the FVII-enriched aqueous phase is centrifuged at 1000 g for 1 hour at 15° C. (centrifuge Sorvall Evolution RC—6700 rpm—rotor SLC-6000). 6 pots of about 835 ml are necessary.

After centrifugation, three phases are present one lipidic phase on the surface (cream), one nonlipidic aqueous clear FVII-enriched phase (majority phase) and one solid white phase in pellet (precipitates of insoluble caseins and of calcium compounds).

The nonlipidic aqueous phase comprising FVII is collected using a persistaltic pump up to the cream phase. The cream phase is recovered separately. The solid phase (precipitate) is removed.

The nonlipidic aqueous phase, however, still comprising very small amounts of lipids, is filtered on a sequence of filters (Pall SLK7002U010ZP—glass fibers prefilter with a pore size of 1 μm—then Pall SLK7002NXP—Nylon 66 with a pore size of 0.45 μm). At the end of filtration, the lipidic phase is passed on this filtration sequence which retains completely the fat globules of the milk, and the filtrate is clear.

The filtered nonlipidic aqueous phase is then dialyzed on an ultrafiltration membrane (Millipore Biomax 50 kDa—0.1 m$^2$) to make it compatible with the chromatographic phase. The FVII with a molecular weight of about 50 kDa does not filter through the membrane, unlike the salts, the sugars and the peptides of the milk. In a first time, the solution (about 5000 ml) is concentrated to 500 ml, then a dialysis by ultrafiltration, maintaining the constant volume, allows to remove the electrolytes and to condition the biological material for the chromatographic step. The dialysis buffer is a 0.025M sodium phosphate buffer, pH 8.2.

This nonlipidic aqueous phase comprising the FVII, can be assimilated to the FVII-tg-enriched lactoserum. This preparation is preserved at −30° C. before continuing the process.

The total yield of the recovery of FVII in this step is very satisfactory: 90% (91% by extraction with phosphate+99% dialysis/concentration).

The nonlipidic aqueous phase comprising the FVII at the end of this step is perfectly clear and compatible with the subsequent chromatographic steps.

About 93000 IU of FVII-tg are extracted at this stage. The purity in FVII of this preparation is of the order of 0.2%.

b) Purification of FVII

1. Chromatography on Hydroxyapatite Gel

An Amicon 90 (9 cm diameter −64 cm$^2$ cross section) column is packed with BioRad Ceramic Hydroxyapatite type I (CHT-I) gel.

The gel is equilibrated with the aqueous buffer A comprising a mixture of 0.025 M sodium phosphate and 0.04 M sodium chloride, pH 8.0. The whole preparation, stored at −30° C., is thawed in a water bath at 37° C. until complete dissolution of the bloc of ice, then is injected onto the gel (linear flow rate 100 cm/h, that is 105 ml/min). The not retained fraction is removed by passage of a buffer comprising 0.025 M sodium phosphate and 0.04 M sodium chloride, pH 8.2, until return to baseline (RBL). Measurements of the absorbance are performed at a wavelength (λ) of 280 nm.

The elution of the fraction containing the FVII-tg is performed with the buffer B comprising 0.25 M sodium phosphate and 0.4 M sodium chloride, pH 8.0. The eluted fraction is collected until return to baseline. Measurements of the absorbance are performed at a wavelength (λ) of 280 nm.

This chromatography allows to recover more than 90% of FVII-tg, while eliminating more than 95% of the lactic proteins. The specific activity (S.A.) is multiplied by 25. At this stage, about 85000 IU of FVII-tg with a purity of 4% are available.

2. 100 kDa Tangential Filtration and 50 kDa Concentration/Dialysis

The whole eluate of the previous step is filtered by tangential mode on a 100 kDa ultrafiltration membrane (Pall OMEGA SC 100K—0.1 m$^2$). The FVII is filtered through the 100 kDa membrane, while the proteins with a molecular weight higher than 100 kDa can not be filtered.

Afterwards, the filtered fraction is concentrated to about 500 ml, then dialyzed on the 50 kDa ultrafilter already described previously. The dialysis buffer is sodium chloride 0.15 M.

At this stage of the process, the product is stored at −30° C., prior to passage in ion-exchange chromatography.

This stage allowed to reduce the load of proteins with a molecular weight higher than 100 kDa and particularly of the pro-enzymes. The treatment on the 100 kDa membrane allows to retain about 50% of proteins, among which the high-molecular weight proteins, while filtering 95% of FVII-tg, that is 82000 IU of FVII-tg.

This treatment allows to reduce the risk of proteolytic hydrolysis during the downstream steps.

3. Chromatographies on Q-Sepharose® FF Gel

These three successive chromatographies on ion exchanger gel Q-Sepharose® Fast Flow (QSFF) are carried out in order to purify the active principle, to allow the activation of FVII to activated FVII (FVIIa) and finally to concentrate and to formulate the composition of FVII. The detection of the compounds is performed through absorbance measurements at λ=280 nm.

3.1 Q-Sepharose® FF 1 Step—Elution «High Calcium»

A 2.6 cm diameter (5.3 cm$^2$ cross section) column is filled up with 100 ml of Q-Sepharose® FF gel (GE Healthcare).

The gel is equilibrated with 0.05 M Tris buffer, pH 7.5.

The whole fraction, stored at −30° C., is thawed in a water bath at 37° C. until complete dissolution of the ice bloc. The fraction is diluted to ½ [v/v] with equilibrating buffer, prior to injection onto the gel (flow rate 13 ml/min, that is a linear flow rate 150 cm/h), then the not-retained fraction is eliminated afterwards by passage of the buffer until RBL.

A first protein fraction having a low content of FVII is eluted at 9 ml/min (that is 100 cm/h) with a 0.05 M Tris and 0.15 M sodium chloride buffer, pH 7.5, and is subsequently removed.

A second FVII-rich protein fraction is eluted at 9 ml/min (that is 100 cm/h) with a 0.05 M Tris and 0.05 M sodium chloride and 0.05 M calcium chloride buffer, pH 7.5.

This second fraction is dialyzed on the 50 kDa ultrafilter already described previously. The dialysis buffer is 0.15 M sodium chloride. This fraction is stored at +4° C. during the night prior to the 2$^{nd}$ passage in anion exchange chromatography.

This stage allows to recover 73% of FVII (that is 60000 IU of FVII-tg), while eliminating 80% of the associated proteins. It allows also the activation of the FVII to FVIIa.

3.2 Q-Sepharose® FF 2 step—Elution «Low Calcium»

A 2.5 cm diameter (4.9 cm$^2$ cross section) column is filled up with 30 ml of Q-Sepharose® FF (GE Healthcare) gel.

The gel is equilibrated with 0.05 M Tris buffer, pH 7.5.

The formerly eluted fraction (second fraction), stored at +4° C., is diluted prior to injection onto the gel (flow rate 9 ml/min, that is a linear flow rate 100 cm/h).

After the injection of the second fraction, the gel is washed with the equilibrating buffer for the removal of the not-retained fraction, until the RLB.

A fraction containing very high purity FVII is eluted at 4.5 ml/min (that is 50 cm/h) in 0.05 M Tris, 0.05 M sodium chloride and 0.005 M calcium chloride buffer, pH 7.5.

About 23000 IU of FVII-tg were purified, that is 12 mg of FVII-tg.

This step allows to eliminate more than 95% of the associated proteins (rabbit milk proteins).

This eluate, with a purity higher than 90%, exhibits the structural and functional features close to those of the natural human FVII molecules. It is concentrated and formulated in the third passage in ion exchange chromatography.

3.3 Q-Sepharose® FF 3 step—«Sodium»Elution

A 2.5 cm diameter (4.9 cm$^2$ cross section) column is filled up with 10 ml of Q-Sepharose® FF gel (GE Healthcare).

The gel is equilibrated with 0.05 M Tris buffer, pH 7.5.

The eluted, purified fraction of the previous step is diluted five times with purified water for injection (PWI) prior to injection onto the gel (flow rate 4.5 ml/min, that is a linear flow rate 50 cm/h).

After the injection of said fraction, the gel is washed with the equilibrating buffer for the removal of the not-retained fraction, until the RLB.

Afterwards, the FVII-tg is eluted with a flow rate 3 ml/min (that is 36 cm/h) with the 0.02 M Tris and 0.28 M sodium chloride buffer, pH 7.0.

A composition of FVII-tg in form of a concentrate was prepared with a purity higher than 95%. The product is compatible with an intravenous injection. The process leads to a cumulated yield of 22%, allowing the purification of at least 20 mg of FVII per liter of milk used.

Further, the FVII-tg of the composition is subjected to different structural analyses such as developed in the following examples.

Example 3: Study of the Primary Sequence

1. Peptide Map

The LC-MS and UV detection chromatograms were obtained after trypsin and Asp-N digestion (data not shown) of the samples of FVII-pd, FVII-rec and FVII-tg.

The analysis of peptide maps obtained after trypsin digestion show that they are similar for retention times less than 65 min. Beyond, species corresponding to peptide fragments of the heavy chain are noticed in the FVII-rec and the FVII-tg and not in the FVII-pd. These peptides having high masses (4500 Da to 8000 Da) are corresponding to abortive cleavages. These peptides were found for other FVII-pd batches, therefore, their presence can not be related to a different trypsin sensibility.

The peptide maps obtained after Asp-N digestion are very similar from one FVII to another, and this along the entire series of retention times. The observed differences in the intensity are due only to variations of injected amounts and are not to be related to structural differences.

2. Covering of Sequence

The overlapping of sequences is computed from the peptides identified by MS and/or MS/MS. Table 1 resumes the results obtained for the different samples. Taking into account the trypsin and Asp-N digestions, more than 95% of the primary sequence could be verified, the obtained results are in accordance with those described in the literature (Thim L. et al, Biochemistry, 1988, 27, 7785-7793).

TABLE 1

Sequence overlaps obtained for the different samples analysed by LC-ESIMS (/MS)

|         | Overlap trypsin (%) | Overlap Asp-N (%) | Global Overlap (%) |
|---------|---------------------|-------------------|--------------------|
| FVII-pd | 79.3                | 97.3              | 97.3               |
| FVII-rec| 97.5                | 95.8              | 100.0              |
| FVII-tg | —                   | 97.0              | 97.0               |
| FVII-tg | 96.6                | 91.1              | 100.0              |
| FVII-tg | 95.3                | 91.1              | 99.0               |

In order to confirm the identity of the peptides, the HPLC fractions were analysed by MALDI and Edman sequencing.

All of the HPLC fractions analysed by Edman sequencing allow to obtain a sequence overlap of 80%. The sequence verifications performed on the FVII-tg and FVII-rec in LC-MS, yield a primary sequence overlap of >95%.

Example 4: Characterization of Glycosylation Sites and of Glycopeptides by ESI-MS The N-glycosylation sites of FVII-tg were identified by LC-ESIMS(/MS), confirmed by MALDI-TOFMS, and the microheterogeneity was determined by LC-ESIMS.

Figure 2:
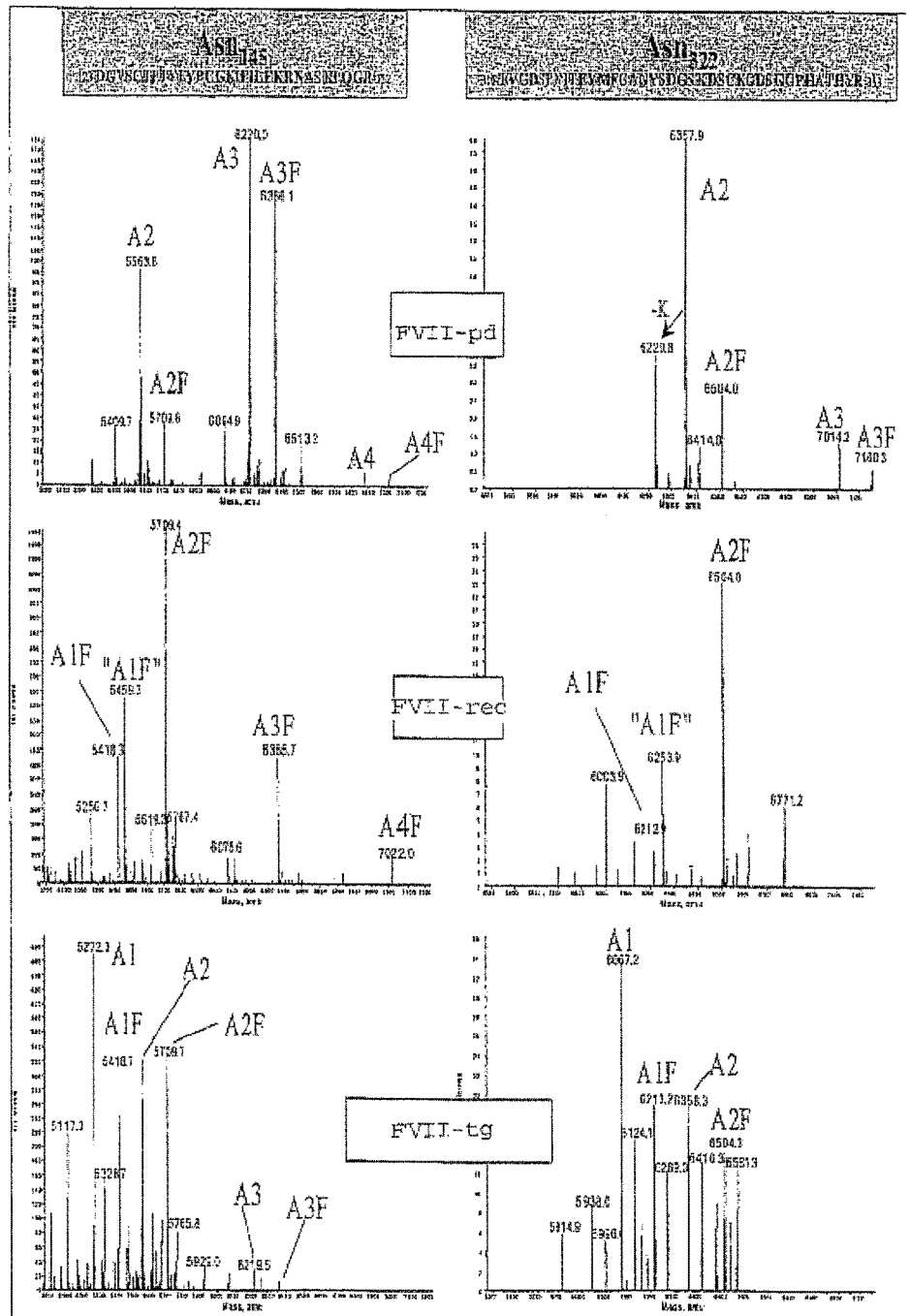
FIG. 2: Deconvoluted mass spectra ESI of peptides carrying the N-glycosylation sites.

FIG. 2 depicts deconvoluted ESI spectra of glycopeptides containing the two glycosylated Asn residues. The position of the glycosylation sites was confirmed by MALDI-TOF(/TOF) and by Edman sequencing, as well.

The analysis of the glycopeptides mass spectra $[D_{123}\text{-}R_{152}]$ and $[K_{31.6}\text{-}R_{353}]$ of plasma FVII (FVII-pd), having the N-glycosylation sites $Asn_{145}$ and $Asn_{322}$ respectively, revealed the presence of biantennary, bisialylated, non-fucosylated structures (A2) (observed mass of glycopeptide: 5563.8 Da) and fucosylated (A2F) (observed mass: 5709.8 Da). Also noted is the presence of triantennary, trisialylated, non-fucosylated oligosaccharides (A3) (observed mass 6220.0 Da) and fucosylated (A3F) (observed mass 6366.1 Da). For the transgenic FVII (FVII-tg), the majority of the oligosaccharides located on the $Asn_{145}$ are of biantennary, monosialylated, non-fucosylated or fucosylated (A1, A1F) and of A2, A2F types. The triantennary forms are poorly represented.

Concerning the majority of $Asn_{322}$ glycoforms, the same glycan structures are observed in different proportions. The FIG. 2 reveals the presence of less processed forms (less antennary and sialylated) than on $Asn_{145}$. For example, the triantennary structures are less represented on $Asn_{322}$ than on $Asn_{145}$ for the plasma product and are lacking on the FVII-tg It should also be noted, that Asn 145 and 322 are glycosylated to 100%. Although semi-quantitative, these results are in accordance with the quantitative values obtained by HPCE-LIF and NP-HPLC.

Example 5: Quantification of N-Glycans by HPCE-LIF

The identification and the quantification of the oligosaccharides N-linked are carried out by HPCE-LIF after deglycosylation by PNGase F. The FVII samples are treated by exoglycosidases (sialidase (ratio Enzyme/Substrate (FVII) 1 mIU/10 µg), galactosidase, hexnacase (kit Prozyme), fucosidase (ratio E/S: 1 mIU/10 µg)) to assure the identification and the quantification of each isolated structure. The obtained glycans are labeled by a fluorochrome and are separated according to their mass and their charge. Two standards (glucose homopolymer and oligosaccharides) allow the structure identifications. The quantification is performed by the integration of each peak with regard to the whole quantified oligosaccharides.

In this example, a capillary electrophoresis ProteoLab PA800 (Beckman-Coulter) device is used, the capillary of which is coated N—CHO (Beckman-Coulter) with a 50 cm×50 µm of intern diameter. A separation buffer named "gel buffer-N" (Beckman-Coulter) is also used. The experiments are performed with 25 kV, 20 min, at 20° C. The detection is carried out using a laser (excitation $\lambda$=488 nm; emission $\lambda$=520 nm.)

The fucosylation proportion is calculated, after simultaneous deglycosylation by sialidase, galactosidase and hexnacase, by the ratio between peak areas corresponding to "core" and fucosylated "core".

Figure 3:
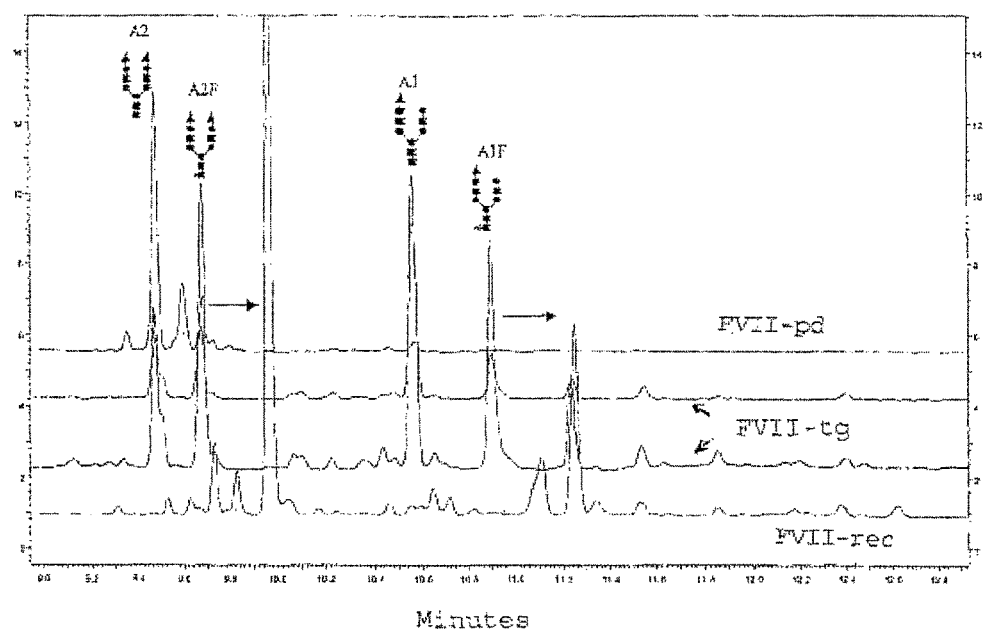
FIG. 3: Electropherograms HPCE-LIF after deglycosylation of the FVII by PNGase F;
Legend: the two electropherograms in center FVII-tg; (◁) fucose, (■) GlcNAc (N-acetylglucosamine), (●) mannose, (●) galactose, (▲) sialic acid.
Electropherogram on top: FVII-pd
Electropherograms in center (2): FVII-tg
Electropherogram on bottom: FVII-rec

The majority of the glycans of FVII-pd are of biantennary, bisialylated (A2), and of biantennary bisialylated, fucosylated (A2F) types. The glycan shapes (see FIG. 3) of the FVII-tg show the presence of structures which are of biantennary, monosialylated, fucosylated or non-fucosylated types (A1F, A1), and are of biantennary, bisialylated, non-fucosylated or fucosylated types (A2, A2F). The shape of the FVII-rec shows atypical migration times for the different observed structures (A1F, A2F).

TABLE 2

Summary of the percentage of sialylated structures resulting from native samples (not desialylated) and those resulting from desialylated samples of the different batches of FVII: FVII-pd and FVII-tg

| Percentage | FVII-pd | FVII-tg batch A | FVII-tg batch B |
|---|---|---|---|
| Native |  |  |  |
| A2 | 41.9 | 19.3 | 13.9 |
| A2F | 8.9 | 14.8 | 21.5 |
| A1 | 2.6 | 38.4 | 25.2 |
| A1F | — | 11.7 | 22.2 |
| Total A2 + A2F | 50.8 | 34.1 | 35.4 |
| Total A1 + A1F | 2.6 | 50.1 | 47.4 |
| Desialylated |  |  |  |
| G2 | 44.5 | 57.5 | 37.2 |
| G2F | 8.9 | 18 | 38.1 |
| G3 | 25 | 4.6 | 3.0 |
| G3F | 5.1 | 1.3 | 3.0 |
| Other non-fucosylated species | 12.6 | 2.9 | 3.0 |

TABLE 2-continued

Summary of the percentage of sialylated structures resulting from native samples (not desialylated) and those resulting from desialylated samples of the different batches of FVII: FVII-pd and FVII-tg

| Percentage | FVII-pd | FVII-tg batch A | FVII-tg batch B |
|---|---|---|---|
| Other fucosylated species | 2.2 | 3.6 | 7.5* |
| G2FB | — | — | — |

*bifucosylated species
G2, G2F: biantennary, bigalactosylated, non-fucosylated or fucosylated forms
G2FB: biantennary, bigalactosylated, bisected, fucosylated forms The quantitative analysis of the different glycan structures (Table 2) reveals the predominance of sialylated structures for the FVII-pd with about 51% of bisialylated glycans (A2 and A2F) and 30% of triantennary, sialylated, non-fucosylated or fucosylated forms (G3 and G3F). The FVII-tg (batches A and B) are less sialylated than the FVII-pd with 35% of biantennary, bisialylated forms and only 6% of triantennary, sialylated forms. The majority of the forms are monosialylated with 50% of structures A1 and A1F. The FVII-rec is also less sialylated than the FVII-pd with 45% of A2F structures and only 6% of triantennary, sialylated, glycans (results not shown).

For the FVII-rec, the low proportion of non-fucosylated structures is noticed.

TABLE 3

Proportion of fucosylation of different FVII

| | FVII-pd | FVII-tg Batch A | FVII-tg Batch B | FVII-rec |
|---|---|---|---|---|
| Proportion of fucosylation (%) | 16.2 | 23.6 | 41.8 | 100 |

Quantitative analysis shows a low proportion of fucosylation of FVII-pd (16%), a proportion of fucosylation from 24 to 42% for the FVII-tg and a fucosylation of 100% for the FVII-rec.

Example 6: Quantification of N-Glycans by NP-HPLC

The qualitative and quantitative analysis of the N-glycosylation of the FVII-pd and the FVII-tg was examined by NP-HPLC. After desalization and drying of the protein, this protein is denatured and reduced according to procedures well-known to the skilled person in the art. Glycans are then released by enzymatic route (endoglycosidase PNGase F) and purified by ethanol precipitation. The thus obtained glycans are labeled by a fluorophore: the 2-aminobenzamide (2-AB). The labeled glycans are separated according to their hydrophilicity using NP-HPLC (Amide-80 column-4,6/250 mm-Tosohaas). Before the injection, the column is equilibrated with 80% acetonitrile. Oligosaccharides are eluted using an increasing gradient of ammonium formate 50 mM, pH 4.5, during time periods equal to or greater than 140 minutes. The detection is performed by fluorometry (Excitation $\lambda$=330 nm; Emission $\lambda$=420 nm).

Figure 4:
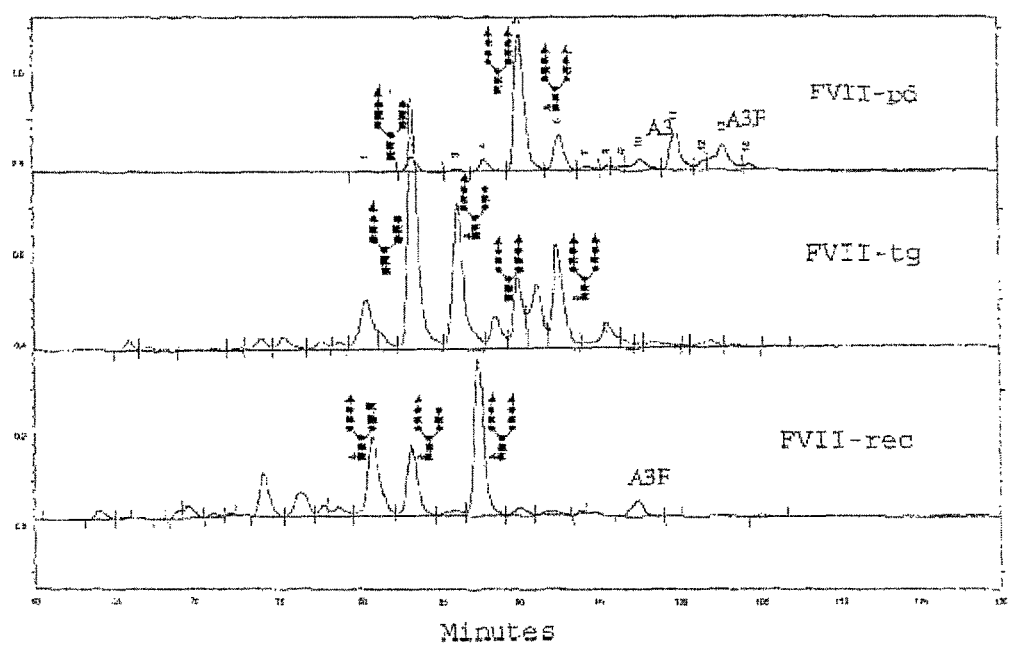
FIG. 4: Characterization of FVII-tg (chromatogram in center) by NP-HPLC, of FVII-pd (chromatogram on top) and of FVII-rec (chromatogram on bottom). Legend of sugar residues: see FIG. 3.

The chromatographic profile (FIG. 4) of FVII-pd shows that the majority of glycans are of biantennary, bisialylated type (A2) with a proportion to 39%. Also are observed, in a lower amount, biantennary, bisialylated, fucosylated (A2F), monosialylated (A1) and trisialylated, fucosylated and non-fucosylated (A3F and A3) forms.

The analysis by NP-HPLC performed on FVII-tg confirms the presence of a majority of oligosaccharides of type A1, up to a proportion of 27%. The structures A1F, A2 and A2F are less represented, and the triantennary forms are present in traces. This reveals a difference of sialylation between the FVII-pd and the less sialylated Factor FVII-tg.

Example 7: Identification by MALDI-TOFMS

Mass Spectrometry MALDI-TOF MS (Matrix—Assisted Laser DEsorption/Ionisation Time of Flight Mass Spectrometry) is a technic allowing to measure the molecular mass of peptides, proteins, glycans, oligonucleotides, and the majority of ionisable polymers with a great precision.

The peptides, proteins and glycans to be analyzed are mixed to a matrix which absorbs at the wavelength of the used laser. The main matrix are $\alpha$-cyano-4-hydroxcinnamic acid (HCCA) for analysing peptides, sinapinic acid (SA) for proteins, and 2,5-dihydroxybenzoic acid (DHB) for oligosaccharides.

The method consists in irradiating matrix/analyte co-crystals with a pulsed laser, resulting in the common desorption of matrix and analyte molecules. After gas phase ionisation, analyte molecules will cross a time of flight detector. Considering that mass and time of flight are directly related, measuring the latter allows to determine the target analyte mass. Identification is performed through observed mass measurements, by comparing with theorical mass. Sequencing can be performed in MS/MS mode, based on the obtained ions fragments. The used apparatus is a Bruker Autoflex 2, functioning in TOF and TOF/TOF modes.

Figure 5:
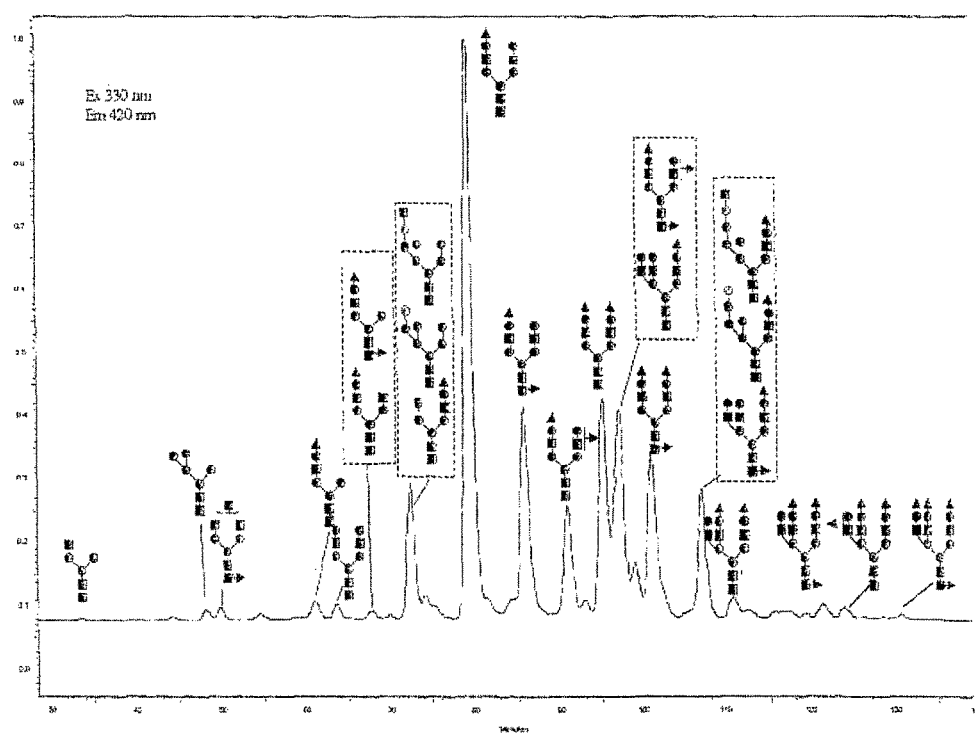
FIG. 5: Identification of the majority of glycan forms of the FVII-tg by MALDI-TOFMS. Legend of sugar residues: see FIG. 3

In order to identify the glycan structures present in the FVII-tg, MALDI-TOF MS analyses were carried out on eluted fractions obtained by preparative NP-HPLC (FIG. 5).

The MALDI-TOF analysis of FVII-tg allowed to confirm the identification of glycans separated by NP-HPLC, namely mostly monosialylated AP1 structures and minority forms of A1F, A2F and A2 type.

This study allowed also to identify the triantennary, bisialylated and trisialylated minority forms, the hybrid forms, and oligomannoses of type Man5 and Man6-P-HexNAc.

In order to identify further glycan structures, a MALDI-TOF MS analysis of Factor FVII-tg is performed after desialylation.

After desialylation, the presence of two majority forms G2 and G2F with a proportion of 35% and of 28%, respectively (quantification by NP-HPLC), is observed. These results are in accordance with the identification of the structures of the «native» product (product not desialylated).

The other identified forms are present in minor amount and are substantially of oligomannose, Man6-P-HexNAc and Man7-P-HexNAc type, and hydride type. The presence of bifucosylated forms is noticed.

Example 8: HPCE-LIF Analysis of the Sialic Acids—Galactose Link

The experimental procedure related to the study of the sialic acid-galactose link ("branching") is similar to the one already described in Example 5. After deglycosylation by PNGase F, the oligosaccharides are treated by specific exosialidases to assure the identification and the quantification of each isolated structure. The used sialidases are recombinant enzymes from *S. pneumoniae* (specific of the $\alpha$2-3 link, 0.02 IU, E/S=0.4 w/w), *C. perfringens* (specific of α2-3 and α2-6 links, 0.04 IU, E/S=0.1 w/w) et *A. urefaciens* (allowing to hydrolyze α2-3, α2-6, α2-8 and α2-9 links, 0.01 IU, E/S=0.05 w/w).

It was shown by analyses that the FVII-rec has biantennary, sialylated, fucosylated glycan structures with a majority of A2F, and biantennary, monosialylated, fucosylated (A1F) forms. Atypical migration times are noted for these structures A2F and A1F comparing with the migration times usually encountered for these structures. Namely, these oligosaccharide sialylated structures exhibit atypical migration times in HPCE-LIF and NP-HPLC compared with those of FVII-tg. On the other hand, the analysis of the composition in monosaccharides did not reveal any particular sialic acid different from Neu5Ac and the mass spectrometry tools reveal glycans with a mass in accordance with the bisialylated types. Finally, the desialylation of glycans of FVII-rec allow to find again chromatographic and electrophoretic behaviours equivalent to those of oligosaccharides of FVII-tg and FVII-pd.

These differences in the electrophoretic and chromatographic behaviour can therefore be explained by a different branching of the sialic acids. This hypothesis was evaluated by different approaches of HPCE-LIF and MS.

The results are resumed in the Table 4 here-below.

TABLE 4

Ramifications of sialic acids in different batches of FVII.

| | Sialylation (%) | α2-3 (%) | α2-6 (%) | α2-8 (%) |
|---|---|---|---|---|
| FVII-pd | 100 | 41 | 59 | 0 |
| FVII-rec | 91 | 100 | 0 | 0 |
| FVII-tg Batch C | 96 | 0 | 100 | 0 |

The results reveal distinctive isomeries at the sialic acids level of the three FVII. Indeed, the sialic acids of FVII-rec imply α2-3 links, while the FVII-tg exhibits ramifications α2-6, and that FVII-pd is a mixture of these two isomers.

The differences in the behaviour in HPCE-LIF and in NP-HPLC observed for the glycans of FVII-rec relatively to FVII-tg and FVII-pd are bound to these isomery differences at the sialic acids level.

Example 9: Study of O-Glycosylation

The FVII presents two O-glycosylation sites located at the $Ser_{52}$ and $Ser_{60}$ level. These residues contain the Glucose-$(Xylose)_{0-2}$ and Fucose moieties, respectively. In the frame of this study, the O-glycosylation was studied by LC-ESIMS (/MS) and in a similar manner by MALDI-TOF(/TOF) (results not shown).

Figure 10:
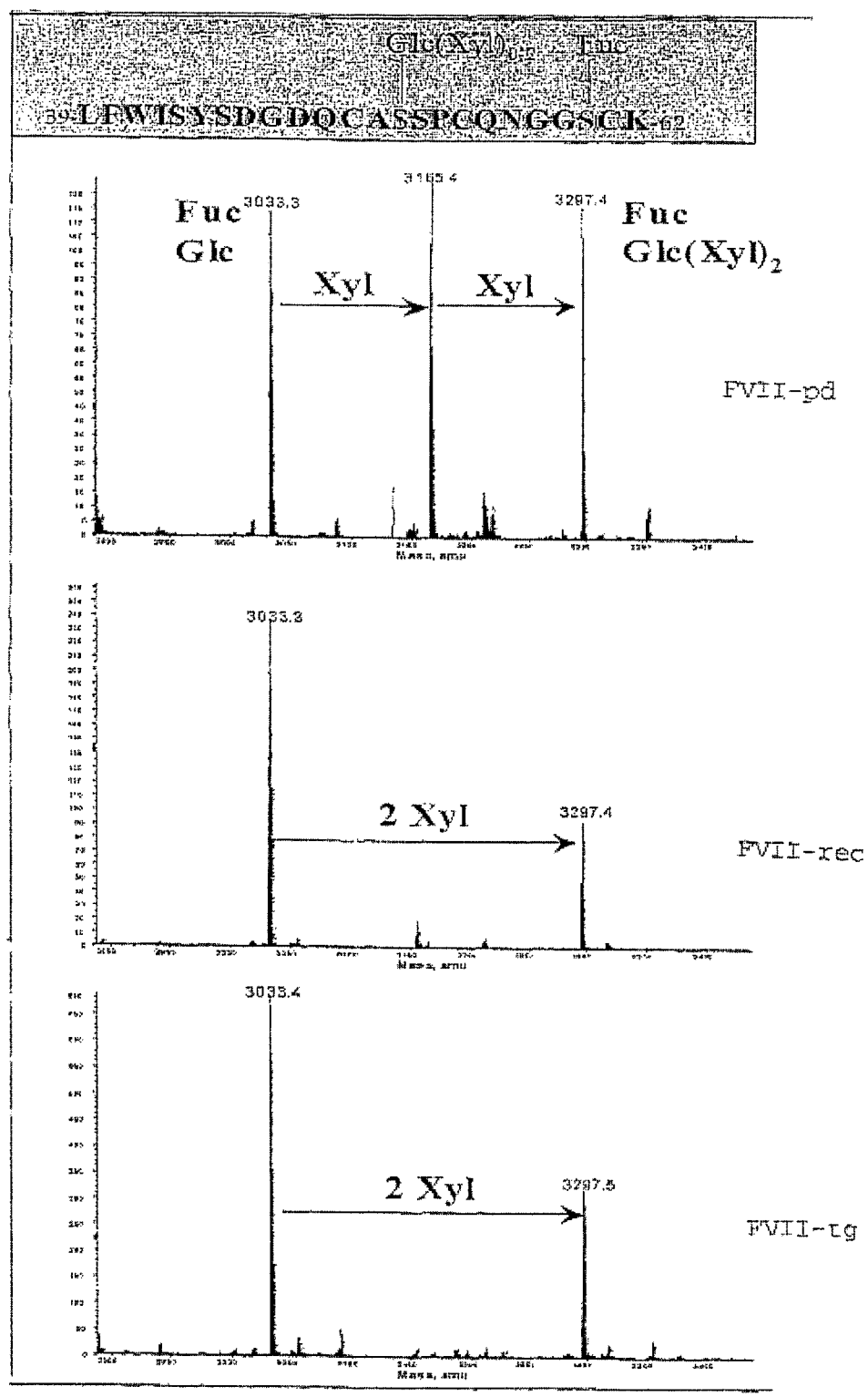
FIG. 10: Deconvoluted mass spectra ESI of peptides carrying the 0-glycosylation sites. These peptides were obtained after digestion with trypsin and by LC-ESIMS analysis. Fuc: fucose, Glc: glucose, Xyl: xylose FIG. 11. Deconvoluted mass spectra ESI of peptides carrying γ-carboxylation sites. These peptides were obtained after digestion with Asp-N and by LC-ESIMS analysis. The obtained results are very similar for the different batches of FVII-tg. The masses of the different peptides are monoisotopic masses. Gla γ-carboxylic acid.

The FIG. 10 illustrates the structures of 0-glycans of the samples FVII-pd, FVII-rec and FVII-tg. The peak at m/z 3297.4 corresponds to the peptide $[Leu_{39}-Lys_{62}]$ comprising the Glucose-$(Xylose)_2$ moieties on the $Ser_{52}$ and Fucose on the $Ser_{60}$. The peaks at m/z 3165.4 and 3033.3 correspond to losses of 1 and 2 xyloses, respectively, on this glycopeptide. The three types of FVII are uniformly fucosylated and glycosylated, but differ in the number of xylose residues, and in the proportion of corresponding glycoforms. Thus, the forms with 0, 1 and 2 xyloses are present in nearly equivalent proportions in the FVII-pd, while the FVII-rec and the FVII-tg comprise only the forms with 0 and 2 xyloses.

The MS analysis shows the double charged ion at m/z 1516.6 corresponding to the peptide $[Leu_{39}-Lys_{62}]$ carrying the structures Fuc and $Glc(Xyl)_0$. The losses of successive masses obtained by MS/MS, which correspond to the different monosaccharides, confirm the modification of the $Ser_{52}$ and $Ser_{60}$ respectively with the glucose and fucose residues. The Edman sequencing allowed to back-up these results in terms of modified sites.

In the same way, the double charged ion at m/z 1648.7 corresponds to the peptide $[Leu_{39}-Lys_{62}]$ carrying the structures Fuc and $Glc(Xyl)_2$. The different ion fragments obtained in MS/MS confirm that the xylose moieties were bound to the Glucose.

Example 10: Study of the γ-Carboxylation

The first 10 glutamic acids of the FVII-pd are γ-carboxylated, while the $10^{th}$ glutamic acid of the FVII-rec is only partially γ-carboxylated. In order to study the γ-carboxylation of the transgenic FVII and of its comparators, peptides obtained after Asp-N and trypsin digestion were analyzed by LC-MS. The conclusions are similar for these two enzymes, only the data relative to the Asp-N digestion are shown.

In these experimental conditions, three peptides $[Ala_1-Lys_{32}]$, $[Asp_{33}-Ser_{45}]$ and $[Asp_{33}-Gly_{47}]$ implying the γ-carboxylation were identified. The peptide $[Ala_1-Lys_{32}]$ contains the first 9 γ-carboxylic acids (Gla) while the two other peptides $[Asp_{33}-Ser_{45}]$ and $[Asp_{33}-Gly_{47}]$ contain only the $10^{th}$ Gla residue. Thus, it is easier to specifically study the partial modification of the $10^{th}$ Gla residue.

The analysis of mass spectra of the FVII-pd (FIG. 11) reveals the presence of a major peak (~90%) at 4296.8 Da, corresponding to the entirely γ-carboxylated peptide $[Ala_1-Lys_{32}]$ on the first 9 glutamic acids (Glu) and a peak at 1658.8 Da characteristic for the completely γ-carboxylated peptide $[Asp_{33}-Ser_{45}]$ at the level of the tenth $Glu_{35}$. These results show, in accordance with the literature (Jurlander B. et al, Semin. Thromb. Hemost., 2001, 27, 373-384), that the first 10 Glu residues of the FVII-pd are γ-carboxylated.

As the different data were obtained under same experimental conditions, a comparative study of the different batches of FVII is possible (Table 5).

Figure 11:
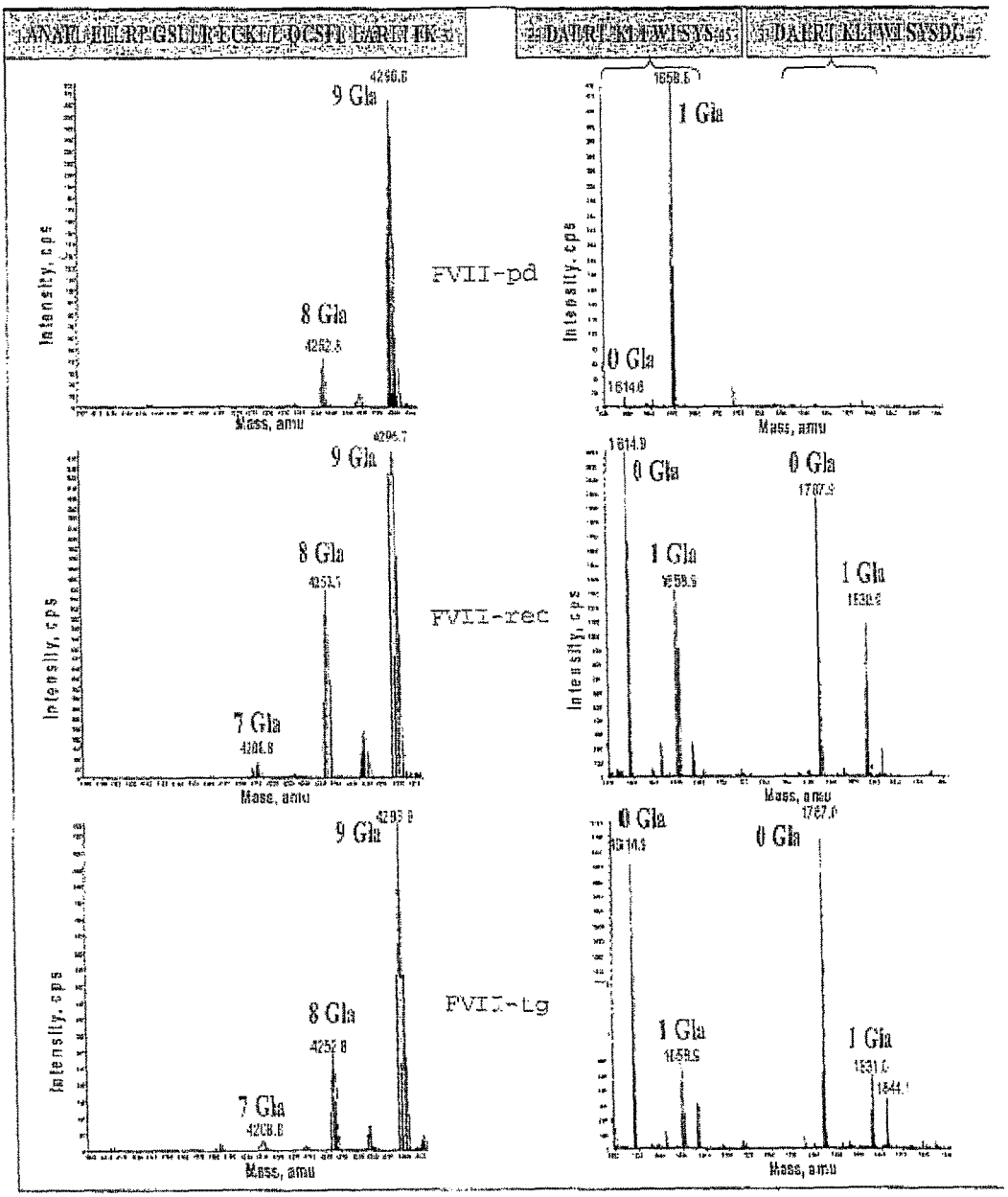

The FIG. 11 shows that for the FVII-rec and FVII-tg, the peak at 4296.8 Da, corresponding to the completely γ-carboxylated peptide $[Ala_1-Lys_{32}]$, is in majority. On the other hand, for both FVII, the presence of a major peak at 1614.9 is seen which represents the characteristic of the not γ-carboxylated peptide $[Asp_{33}-Ser_{45}]$ on the Gla35. This result indicates a partial γ-carboxylation of the $10^{th}$ Gla evaluated to about 35-40% in the case of the FVII-rec, what is in accordance with the published value of ~50% (Thim L. et al, Biochemistry, 1988, 27, 7785-7793 and Jurlander B. et al, Semin. Thromb. Hemost., 2001, 27, 373-383). The presence of a form with 8 Gla with a non negligible intensity in the peptide $[Ala_1-Lys_{32}]$ should also be reported. This last point indicates a partial γ-carboxylation of one or more Gla in this peptide, the presence of "traces" of a form with 7 Gla would rather emphasize the involvement of a single residue.

TABLE 5

Summary of data concerning the γ-carboxylation of Glu. These data are resulting from the LC-ESIMS analysis.

| | Number of Gla residues | Majority form (n Gla) |
|---|---|---|
| FVII-pd | 8-10 | 10 |
| FVII-rec | 7-10 | 9 |

TABLE 5-continued

Summary of data concerning the γ-carboxylation of Glu. These data are resulting from the LC-ESIMS analysis.

| | Number of Gla residues | Majority form (n Gla) |
|---|---|---|
| FVII-tg | 7-10 | 9 |
| FVII-tg | 7-10 | 9 |

Gla: γ-carboxylic acid.

Example 11: Study of Disulfide Bridges

The study of disulfide bridges of the FVII was carried out from the trypsic hydrolysate obtained in non reductant conditions, i.e that the disulfide bridges are maintained.

A reaction step with iodacetamid was included in order to block the possible free cysteins, and thus to avoid an exchange of disulfide bridges during the steps carried out at a basic pH.

Under these conditions, it was possible to confirm the existence of 12 disulfide bridges and to pair 10 cysteins (Table 6). However, it should be emphasized, that the obtained results relative to this part of the sequence of FVII, are in accordance with the theoretical pairing. These conclusions are applicable to both investigated samples: FVII-pd and FVII-tg.

TABLE 6

Summary of results obtained in the disulfide bridges study

| | FVII-pd | FVII-tg |
|---|---|---|
| CONFIRMED DISULFIDE BRIDGES | 12 | 12 |
| Paired cysteins | $Cys_{17}$-$Cys_{22}$ | $Cys_{17}$-$Cys_{22}$ |
| | $Cys_{114}$-$Cys_{127}$ | $Cys_{114}$-$Cys_{127}$ |
| | $Cys_{135}$-$Cys_{262}$ | $Cys_{135}$-$Cys_{262}$ |
| | $Cys_{159}$-$Cys_{164}$ | $Cys_{159}$-$Cys_{164}$ |
| | $Cys_{178}$-$Cys_{194}$ | $Cys_{178}$-$Cys_{194}$ |
| | $Cys_{310}$-$Cys_{329}$ | $Cys_{310}$-$Cys_{329}$ |
| | $Cys_{340}$-$Cys_{368}$ | $Cys_{340}$-$Cys_{368}$ |

The used experimental strategy is applied to a dipeptide $[Gly_{354}$-$Ser_{379}]/[Asp_{338}$-$Lys_{341}]$ without any post-translational modifications (MPT) (Results not shown). This strategy implies 4 complementary approaches: i) identification of dipeptides containing the disulfide bridges by double "matching" of masses by ESI-MS and MALDI-MS between the experimental and observed masses, ii) confirmation of structures by chemical reduction of S-S bridges, and MS identification of the two peptides generated from the dipeptide and iii) the sequencing of the dipeptides by MS/MS and automatic Edman microsequencing.

The results show a first identification of the dipeptide $[Gly_{354}$-$Ser_{379}]/[Asp_{338}$-$Lys_{341}]$ implying a disulfide bridge $Cys_{340}$-$Cys_{368}$ by «matching» of the experimental mass (3264.6 Da) with the theoretical mass (3264.5 Da).

After reduction, the disappearance of the peak corresponding to this dipeptide $[Gly_{354}$-$Ser_{379}]/[Asp_{338}$-$Lys_{341}]$ containing the bridge $Cys_{340}$-$Cys_{368}$ is noticed in the favour of a peak at m/z 2816.3 characteristic of the peptide $[Gly_{354}$-$Ser_{379}]$ (theoretical mass: 2816.3 Da) containing the $Cys_{368}$. The sequencing by MS/MS and by Edman chemistry confirms the identification of the dipeptide $[Gly_{354}$-$Ser_{379}]/[Asp_{338}$-$Lys_{341}]$ and of the disulfide bridge $Cys_{340}$-$Cys_{368}$.

Example 12: Study of the β-Hydroxylation of the Aspartic Acid 63

The peptide analysis is carried out from a trypsic "digest" of the protein. Peptides are analysed by MALDI-MS. The identification of hydroxylated peptides is performed by a measurement of the observed mass compared to the theoretical mass. The apparatus used is a Bruker Autoflex 2 running according to TOF mode.

The different results are presented in the Table 7. It should be emphasized that the literature reports the absence of β-hydroxylation of FVII-pd and FVII-rec (Thim L. et al, Biochemistry, 1988, 27, 7785-7793), while a partial modification of both these samples could be observed, however in a less abundant fashion than in the different FVII-tg batches.

TABLE 7

Summary of data concerning the hydroxylation of the $Asp_{63}$. These data result from the LC-ESIMS analysis of the trypsic peptides.

| | Hydroxylation $Asp_{63}$ |
|---|---|
| FVII-pd | Partial* |
| FVII-rec | Non** |
| FVII-tg | Partial |
| FVII-tg | Partial |
| FVII-tg | Partial |

*β-hydroxylation less "abundant" than the FVII-tg.
**Value cited in Thim L. et al, Biochemistry, 1988, 27, 7785-7793)

Example 13: Study of the Presence of Galα1,3Gal Structures

In order to study the possible presence of the Galα1,3Gal structures in the FVII-tg, use is made of bovine thyroglobulin as positive control of the Galα1,3Gal structures.

The products are, after deglycosylation with PNGase F, treated with Galα1,3Gal branchment-specific sialidase, fucosidase and α-galactosidase.

Figure 6:
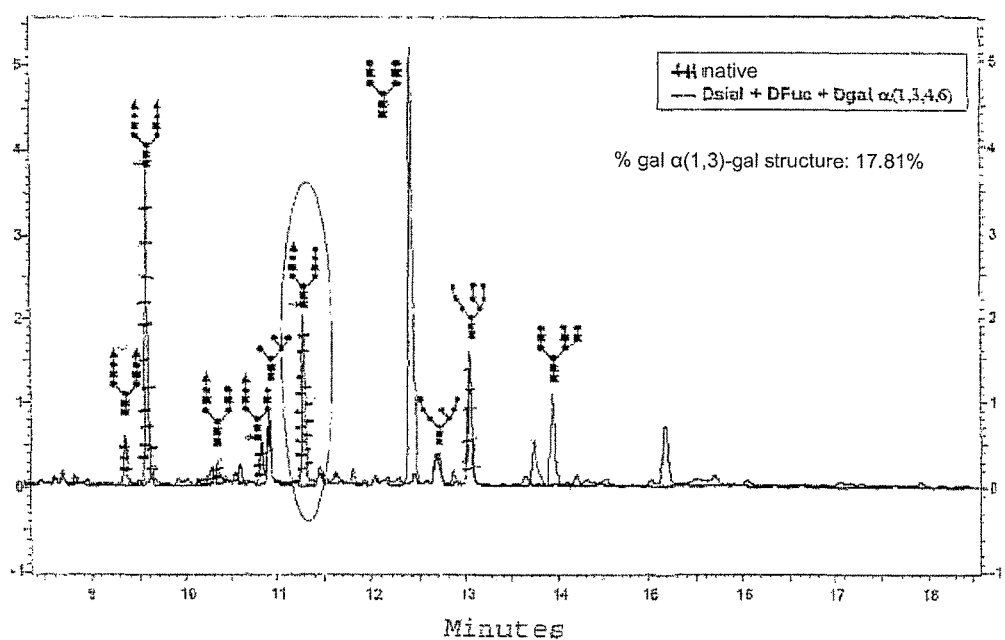
FIG. 6: Analysis by HPCE-LIF of the oligosaccharides of thyroglobulin. Legend of sugar residues: see FIG. 3

The FIG. 6 illustrates the study carried out on bovine thyroglobulin with superposition of the native shape ("Natif") and of desialylated, defucosylated and α-degalactosylated shape (Dsial+Dfuc+Dgalα(1,3,4,6)). The glycan shape obtained after the α-degalactosylation shows that this structure completely disappears after treatment with the enzyme, thus proving that the used α-galactosidase is perfectly active. The proportion of the obtained Galα1,3Gal structure of 17.8% is coherent with the expected proportion.

Figure 7:
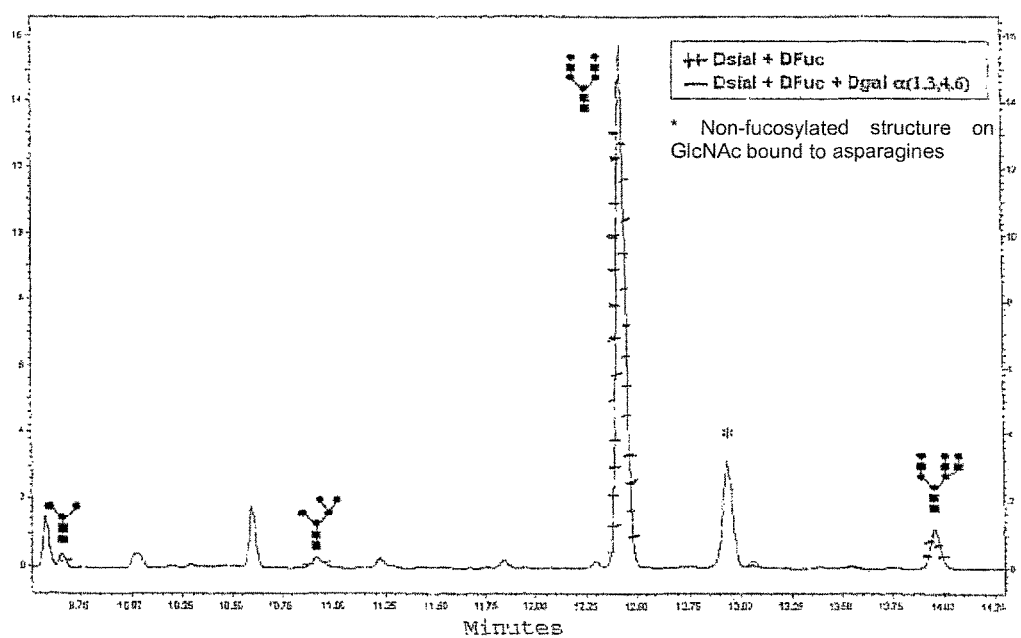
FIG. 7: Analysis by HPCE-LIF of the oligosaccharides of transgenic FVII. Legend of sugar residues: see FIG. 3

The FIG. 7 illustrates the superposition of electrophoregrams of the desialylated and defucosylated FVII-tg product (Dsial+Dfuc) with desialylated, defucosylated and α-degalactosylated product (Dsial+Dfuc+Dgalα(1,3,4,6)).

It is noted that both shapes are perfectly superposable. These results suggest the absence of Galα1,3Gal structures in the FVII-tg. It should be noticed the presence of minority structures (*) corresponding to glycans fucose of which is not in proximal position.

Example 14: Quantification of Galα1,3Gal Saccharide Moieties

10 μg of human recombinant and transgenic FVII, were treated according to disulfide briges reduction conditions, deposited on electrophoresis gel and transferred onto a nitrocellulose membrane. A sample of bovine thyroglobulin (Sigma, T1001, Thyroglobulin from bovin thyroid) is used as positive control because of its high epitope alpha(1,3) galactosyl content. The presence of the α-Gal moiety (Galactose-alpha1-3Galactose-(3)4GlcNAc-R) is revealed with purified lectin *Marasmius oreades* agglutinin peroxydase-labelled and α-Gal epitope-specific (EY Laboratories, H-9001, MOA-HRP). Afterwards, the peroxydase activity is detected with a chromogenic substrate (Fluke, 4-chloro-1-naphthol) and quantified by signal digitalisation (Bio-Rad, Quantity-one). An identical membrane is treated with an alpha-galactosidase (Prozyme, Green coffee bean) in order to confirm the signal specificity. At the same time, the total protein amount is also evaluated by staining of an identical SDS-PAGE gel, stained with Coomassie blue.

The results show the specificity of the lectin *Marasmius oreades* (MOA) as a result of the strong signal observed for the bovine thyroglobulin and of its disappearance following the treatment with an alpha-galactosidase. The results expressed in relation to the intensity of the MOA signal divided by the intensity of the signal corresponding to the amount of the analysed protein, demonstrate a level of the residual α-Gal signal (2,3 à 3,7) for the sample of FVII-tg, while the recombinant FVII exhibits a higher value.

Figure 8:
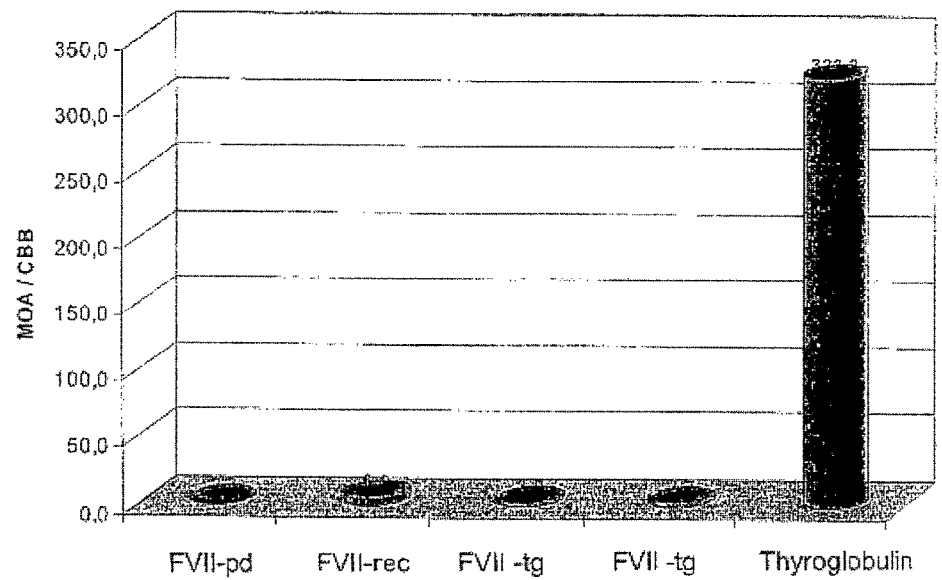
FIG. 8: Quantification of the Galα1,3Gal structures
Figure 9:
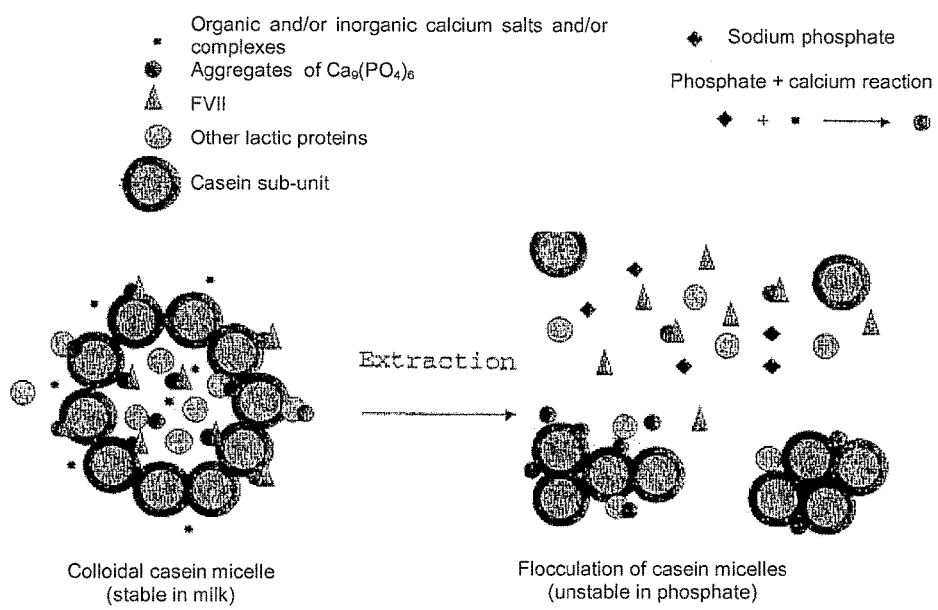
FIG. 9: Example of an extraction mechanism of the FVII

These results (see FIG. 8) demonstrate the absence or the very weak prevalence of the α-Gal epitope on the transgenic FVII expressed in rabbit, compared to a recombinant FVII product in hamster cells, for example.

The Table A resumes the process steps according to a preferred embodiment of the invention in order to provide for the composition of FVII of the invention, and provides for the different yields, the purity and the specific activities obtained in each step.

TABLE A

| Batch N° 479030 | Volume (ml) | Amount of protein (mg) | Amount of FVII: Ag (U) | FVII Yld/ step (%) | FVII Yld/ cumul. (%) | AS (U/mg) | FVII purity (%) |
|---|---|---|---|---|---|---|---|
| Pooled whole milk | 500 | 42750 | 103450 | 100% | 100% | 2.4 | 0.12% |
| Phosphate clarification | 4785 | ND | 93650 | 91% | 91% | — | — |
| Concentration/dialysis (50 kD UF) | 667 | 29610 | 93233 | 99% | 90% | 3.1 | 0.20% |
| Hydroxyapatite Eluate (CHT-I) | 2644 | 1071 | 85692 | 92% | 79% | 80.0 | 4.0% |
| Tangential filtration (100 kD UF) | 459 | 518 | 81684 | 95% | 72% | 157.6 | 7.9% |
| QSFF1 eluate (high Ca$^{2+}$) | 402 | 105 | 59757 | 73% | 58% | 572 | 28.6% |
| QSFF2 eluate (low Ca$^{2+}$) | 157 | 12.8 | 22447 | 38% | 22% | 1749 | 87% |
| QSFF3 eluate (sodium) | 42.5 | 12.7 | 21929 | 98% | 21% | 1727 | 86% |
| Finished product (0.2 µm sterilisation) | 50 | 12.4 | 23197 | 106% | 22% | 1878 | 94% |

Yld: yield

The invention claimed is:

1. A composition comprising recombinant human Factor VII (FVII) produced by a transgenic female rabbit,
wherein each molecule of FVII of the composition exhibits glycan moieties and two N-glycosylation sites,
wherein among all the molecules of FVII of the composition, the proportion of Galα1,3Gal glycan moieties is between 0 and 4%,
wherein among all the molecules of FVII of the composition, all sialic acids of the FVII are bound in α2-6 links,
wherein among all the glycan moieties bound to N-glycosylation sites of the FVII of the composition, more than 50% of the glycan moieties are biantennary, monosialylated, glycan moieties,
wherein the molecules of FVII of the composition exhibit nine γ-carboxylated N-terminal glutamic acids, and
wherein the molecules of FVII of the composition exhibit 12 specific disulfide bridges.

2. The composition according to claim 1, wherein among all the glycan moieties of the FVII of the composition, at least 60% are biantennary, monosialylated, glycan moieties.

3. The composition according to claim 2, wherein among the biantennary, monosialylated glycan moieties of the FVII, more than 50% of the glycan moieties are non-fucosylated.

4. The composition according to claim 3, wherein the proportion of fucosylation of Factor VII is between 20% and 50%.

5. The composition of Factor VII according to claim 1, further comprising a pharmaceutically acceptable excipient or carrier.

6. A method for treating haemophilia comprising administering to a patient in need thereof, a therapeutic dose of a composition comprising recombinant Factor VII (FVII) produced by a transgenic female rabbit, and a pharmaceutically acceptable excipient or carrier,
- wherein each molecule of FVII of the composition exhibits glycan moieties and two N-glycosylation sites,
- wherein among all the molecules of FVII of the composition, the proportion of Galα1,3Gal glycan moieties is between 0 and 4%,
- wherein among all the molecules of FVII of the composition, all sialic acids of the FVII are bound in α2-6 links,
- wherein among all the glycan moieties bound to N-glycosylation sites of the FVII of the composition, more than 50% of the glycan moieties are biantennary, monosialylated, glycan moieties,
- wherein the molecules of FVII of the composition exhibit nine y-carboxylated N-terminal glutamic acids, and
- wherein the molecules of FVII of the composition exhibit 12 specific disulfide bridges.

7. A method for treating multiple hemorrhagic traumas comprising administering to a patient in need thereof, a therapeutic dose of a composition comprising recombinant Factor VII (FVII) produced by a transgenic female rabbit, and a pharmaceutically acceptable excipient or carrier,
- wherein each molecule of FVII of the composition exhibits glycan moieties and two N-glycosylation sites,
- wherein among all the molecules of FVII of the composition, the proportion of Galα1,3Gal glycan moieties is between 0 and 4%,
- wherein among all the molecules of FVII of the composition, all sialic acids of the FVII are bound in α2-6 links,
- wherein among all the glycan moieties bound to N-glycosylation sites of the FVII of the composition, more than 50% of the glycan moieties are biantennary, monosialylated, glycan moieties,
- wherein the molecules of FVII of the composition exhibit nine y-carboxylated N-terminal glutamic acids, and
- wherein the molecules of FVII of the composition exhibit 12 specific disulfide bridges.

8. A method for treating incontrollable massive bleedings by surgical haemostasis comprising administering to a patient in need thereof, a therapeutic dose of a composition comprising recombinant Factor VII (FVII) produced by a transgenic female rabbit, and a pharmaceutically acceptable excipient or carrier,
- wherein each molecule of FVII of the composition exhibits glycan moieties and two N-glycosylation sites,
- wherein among all the molecules of FVII of the composition, the proportion of Galα1,3Gal glycan moieties is between 0 and 4%,
- wherein among all the molecules of FVII of the composition, all sialic acids of the FVII are bound in α2-6 links,
- wherein among all the glycan moieties bound to N-glycosylation sites of the FVII of the composition, more than 50% of the glycan moieties are biantennary, monosialylated, glycan moieties,
- wherein the molecules of FVII of the composition exhibit nine y-carboxylated N-terminal glutamic acids, and
- wherein the molecules of FVII of the composition exhibit 12 specific disulfide bridges.

9. A method for treating of bleedings or haemorrhages due to an overdose of anticoagulants comprising administering to a patient in need thereof, a therapeutic dose of a composition comprising recombinant Factor VII (FVII) produced by a transgenic female rabbit, and a pharmaceutically acceptable carrier,
- wherein each molecule of FVII of the composition exhibits glycan moieties and two N-glycosylation sites,
- wherein among all the molecules of FVII of the composition, the proportion of Galα1,3Gal glycan moieties is between 0 and 4%,
- wherein among all the molecules of FVII of the composition, all sialic acids of the FVII are bound in α2-6 links,
- wherein among all the glycan moieties bound to N-glycosylation sites of the FVII of the composition, more than 50% of the glycan moieties are biantennary, monosialylated, glycan moieties,
- wherein the molecules of FVII of the composition exhibit nine y-carboxylated N-terminal glutamic acids, and
- wherein the molecules of FVII of the composition exhibit 12 specific disulfide bridges.

10. The composition according to claim 1, wherein the Factor VII is activated.

* * * * *